US011117996B2

(12) United States Patent
Morita et al.

(10) Patent No.: US 11,117,996 B2
(45) Date of Patent: Sep. 14, 2021

(54) SELF-ASSEMBLY COMPOSITION FOR PATTERN FORMATION AND PATTERN FORMING METHOD

(71) Applicant: Oji Holdings Corporation, Tokyo (JP)

(72) Inventors: Kazuyo Morita, Tokyo (JP); Kimiko Hattori, Tokyo (JP)

(73) Assignee: OJI HOLDINGS CORPORATION, Tokyo (JP)

(*) Notice: Subject to any disclaimer, the term of this patent is extended or adjusted under 35 U.S.C. 154(b) by 0 days.

(21) Appl. No.: 16/303,285

(22) PCT Filed: Feb. 27, 2017

(86) PCT No.: PCT/JP2017/007321
§ 371 (c)(1),
(2) Date: Nov. 20, 2018

(87) PCT Pub. No.: WO2017/199521
PCT Pub. Date: Nov. 23, 2017

(65) Prior Publication Data
US 2019/0211130 A1  Jul. 11, 2019

(30) Foreign Application Priority Data

May 20, 2016 (JP) .............................. JP2016-101455

(51) Int. Cl.
*C08F 293/00* (2006.01)
*H01L 21/027* (2006.01)
(Continued)

(52) U.S. Cl.
CPC ........... *C08F 293/005* (2013.01); *C07H 5/04* (2013.01); *C08F 293/00* (2013.01);
(Continued)

(58) Field of Classification Search
CPC ...... B21C 37/06; B21C 37/154; F02M 55/02; F16L 58/184; F16L 9/04; Y10T 29/49927;
(Continued)

(56) References Cited

U.S. PATENT DOCUMENTS 9,377,684 B2   6/2016  Aissou et al.
2011/0281934 A1*  11/2011  Johnson ............... A61K 9/1075
514/44 A
(Continued)

FOREIGN PATENT DOCUMENTS

CN   103946254 A   7/2014
CN   104829847 A   8/2015
(Continued)

OTHER PUBLICATIONS

Japanese Office Action dated May 7, 2019 issued in the corresponding Japanese patent application No. 2019-025195 with its English Machine Translation.
(Continued)

*Primary Examiner* — Lan Vinh
(74) *Attorney, Agent, or Firm* — Browdy and Neimark, PLLC

(57) ABSTRACT

It is an object of the present invention to provide a self-assembly composition for pattern formation having a wide range of applicable pattern size and being capable of forming a favorable phase-separated structure. The present invention relates to a self-assembly composition for pattern formation, which comprises a block copolymer comprising a polymerization unit (a) having at least one selected from a structure represented by the following formula (103) and a structure represented by the following formula (104), and a polymerization unit (b) having a structure represented by
(Continued)

the following formula (105), wherein the content rate of a sugar moiety in the block copolymer is 3% by mass or more and 80% by mass or less based on the total mass of the block copolymer:

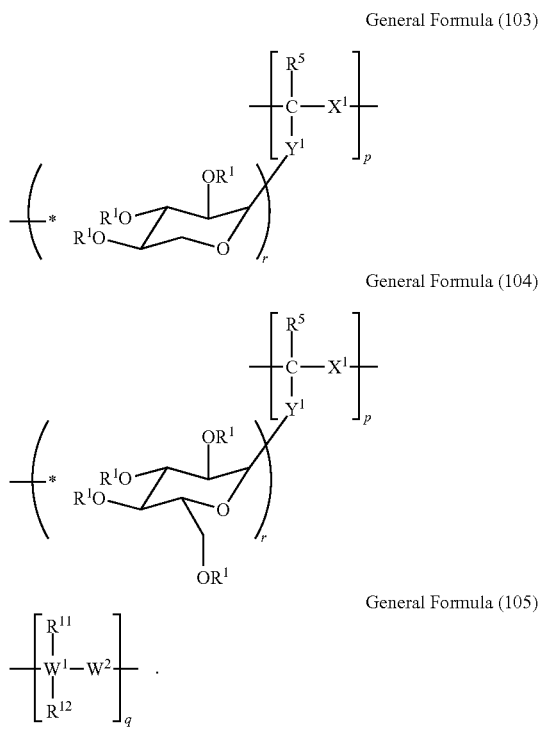

9 Claims, 4 Drawing Sheets

(51) Int. Cl.
*C07H 5/04* (2006.01)
*H01L 21/311* (2006.01)
(52) U.S. Cl.
CPC ...... *H01L 21/027* (2013.01); *H01L 21/31138* (2013.01); *C08F 2438/01* (2013.01); *Y02P 20/54* (2015.11)
(58) Field of Classification Search
CPC . Y10T 29/49934; C07H 5/04; C08F 2438/01; C08F 293/00; C08F 293/005; H01L 21/027; H01L 21/31138; Y02P 20/542; Y02P 20/54; C09K 13/06; B81C 1/00031
USPC ........ 252/79.1, 79.2, 79.3, 79.4; 430/108.15, 430/296, 297, 313
See application file for complete search history.

(56) References Cited

U.S. PATENT DOCUMENTS

2013/0022785 A1\* 1/2013 Ellison ................ C08B 37/0006
428/141
2014/0179624 A1\* 6/2014 Gutterman .............. A61P 35/00
514/33
2014/0193337 A1\* 7/2014 Schibli ................ A61K 51/0491
424/1.73
2015/0238597 A1\* 8/2015 Seeberger ............... A61P 31/22
424/194.1

FOREIGN PATENT DOCUMENTS

| CN | 109071823 A | 12/2018 |
| EP | 3395859 A1 | 10/2018 |
| JP | 62-220505 A | 9/1987 |
| JP | S63-238105 A | 10/1988 |
| JP | 02275892 A | 11/1990 |
| JP | H08-104651 A | 4/1996 |
| JP | H11-035592 A | 2/1999 |
| JP | 2001-502304 A | 2/2001 |
| JP | 2002-343381 A | 11/2002 |
| JP | 2004124088 A | 4/2004 |
| JP | 2005-341960 A | 12/2005 |
| JP | 2008-012460 A | 1/2008 |
| JP | 2010-91630 A | 4/2010 |
| JP | 2010-091630 A | 4/2010 |
| JP | 2013-510588 A | 6/2013 |
| JP | 2013539420 A | 10/2013 |
| JP | 2014005325 A | 1/2014 |
| JP | 2014527089 A | 10/2014 |
| JP | 2016079242 A | 5/2016 |
| KR | 10-2015-0046209 A | 11/2016 |
| TW | 201428046 A | 7/2014 |
| WO | 1998/12203 A1 | 3/1998 |
| WO | 2006070841 A1 | 7/2006 |
| WO | 2012/177839 A1 | 12/2012 |
| WO | 2016060077 A1 | 4/2016 |
| WO | 2017-110190 A1 | 6/2017 |

OTHER PUBLICATIONS

Japanese Office Action dated Jan. 8, 2019 issued in the corresponding Japanese patent application No. 2018-518102 with its English Machine Translation.
Office Action dated Oct. 28, 2019 issued in the corresponding Korean patent application No. 10-2018-7035045 with its English Machine Translation.
Extended European Search Report dated Feb. 21, 2020 issued in the corresponding European patent application No. 17798959.7.
Narumi A et al, Synthesis of amphiphilic triblock copolymer of polystyrene and poly(4--vinylbenzyl glucoside) via TEMPO-mediated living radical polymerization, Polymer, 43:4835-4840 (2002).
Narumi et al., Glycoconjugated polymer: Synthesis and characterization of poly(vinyl saccharide)-block-polystyrene-block-poly(vinyl saccharide) as an amphiphilic ABA triblock copolymer, Journal of Polymer Science: Part A: Polymer Chemistry, 44:3978-3985 (2006).
Zi-Chen Li et al., Synthesis of amphiphilic block copolymers with well-defined glycopolymer segment by atom transfer radical polymerization, Macromol. Rapid Commun, 21:375-380 (2000).
Yu-Zeng Liang et al., Multiple morphologies of molecular assemblies formed by polystyrene-block-poly[2β-D-glucopyranosyloxy)ethyl acrylate] in water (2000).
Harrison et al., Lithography with Self-Assembled Block Copolymer Microdomains, Developments in Block copolymer Science and Technology (2004).
Office Action dated Mar. 12, 2020 issued in the corresponding Korean patent application No. 10-2018-7035045 with its English Machine Translation.
Notice of Reasons for Refusal dated Sep. 3, 2019 in corresponding Japanese application No. 2019-025195.
Toshiba Review., "Directed Self-Assembly Lithography Technology" vol. 67, No. 4, pp. 44-4, (2012) with its English translation.
International Search Report and Written Opinion of PCT/JP2017/007321, dated May 16, 2017.
International Preliminary Report on Patentability of Chapter I with its English translation, Nov. 29, 2018.
Office Action dated Jun. 23, 2020 issued in the corresponding Chinese patent application No. 201780030987.3 with its English Machine Translation.
Shen, Yulong, "China Environmental Science Press", Green Chemistry, Version 3 (Publication date: Apr. 30, 2016), p. 41.

(56) References Cited

OTHER PUBLICATIONS

Zhang, Jun, "Gansu Cultural Press", Green Coordination Catalysis, (Publication date: Nov. 30, 2009), pp. 54-55.
Office Action dated Sep. 18, 2020 issued in the corresponding Taiwanese patent application No. 106106403 with its English Machine Translation.
Office Action dated May 8, 2021 issued in the corresponding Chinese patent application No. 201780030987.3 with its English Translation.

* cited by examiner

[Figure 1]
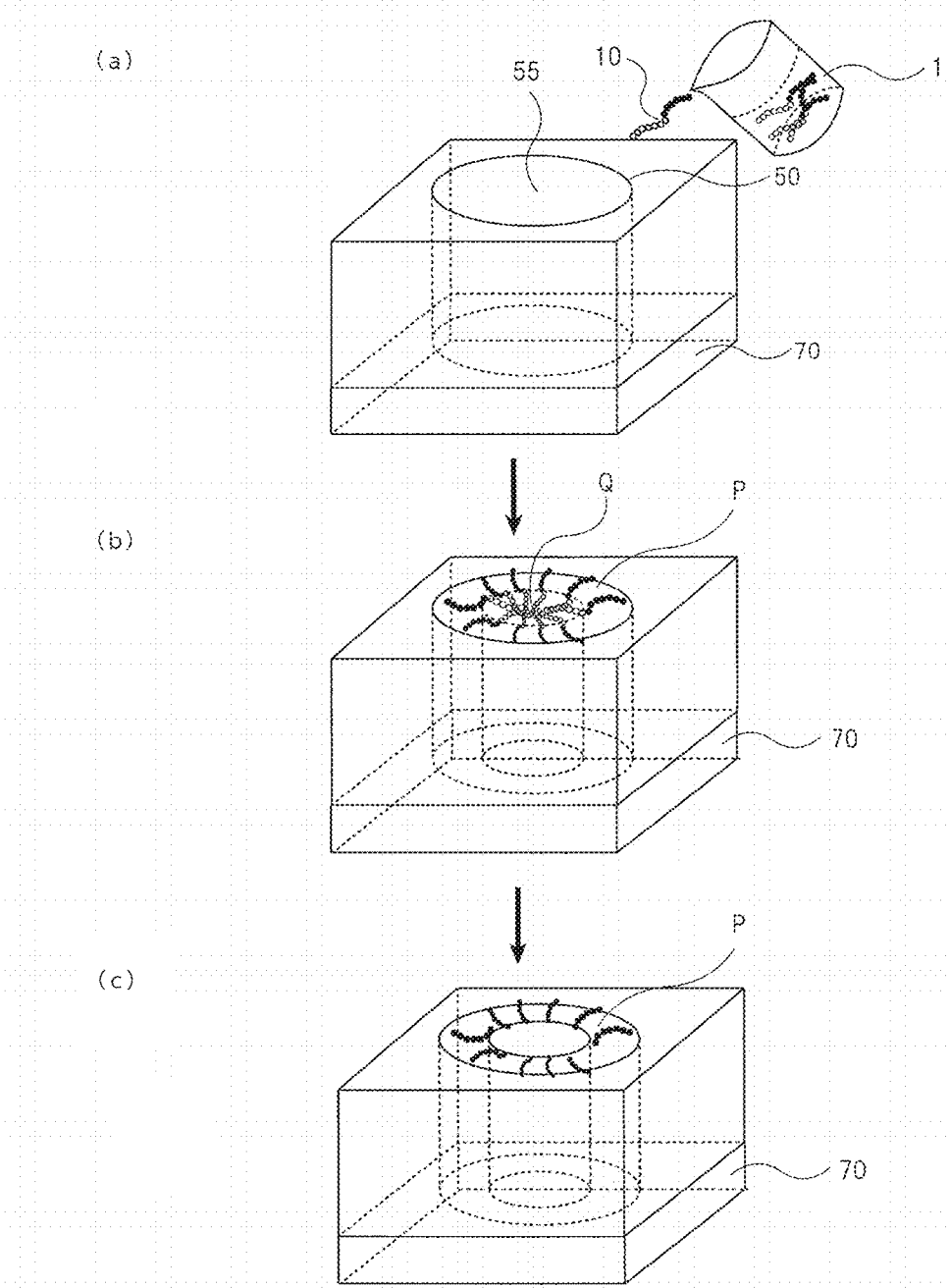

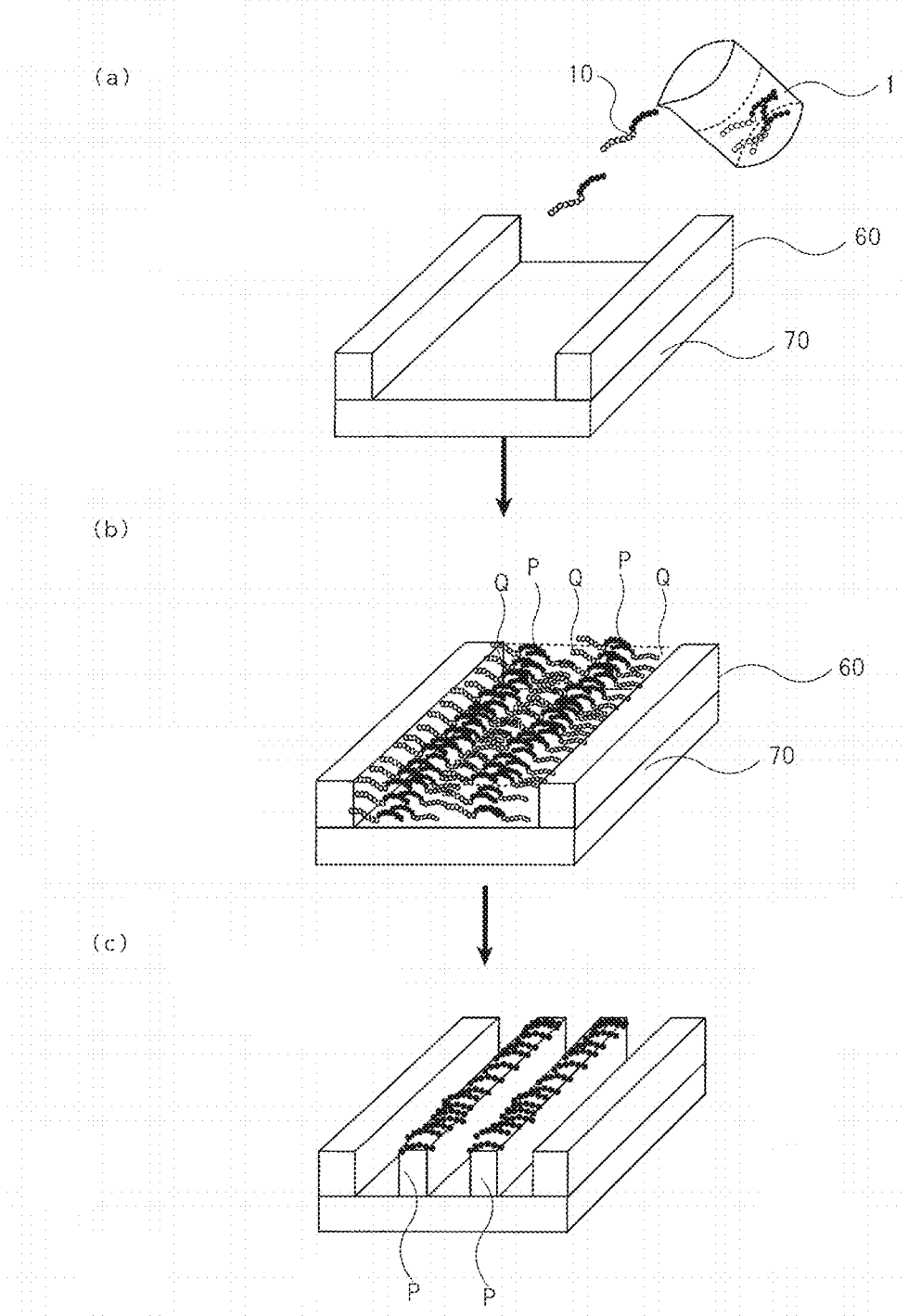
[Figure 2]

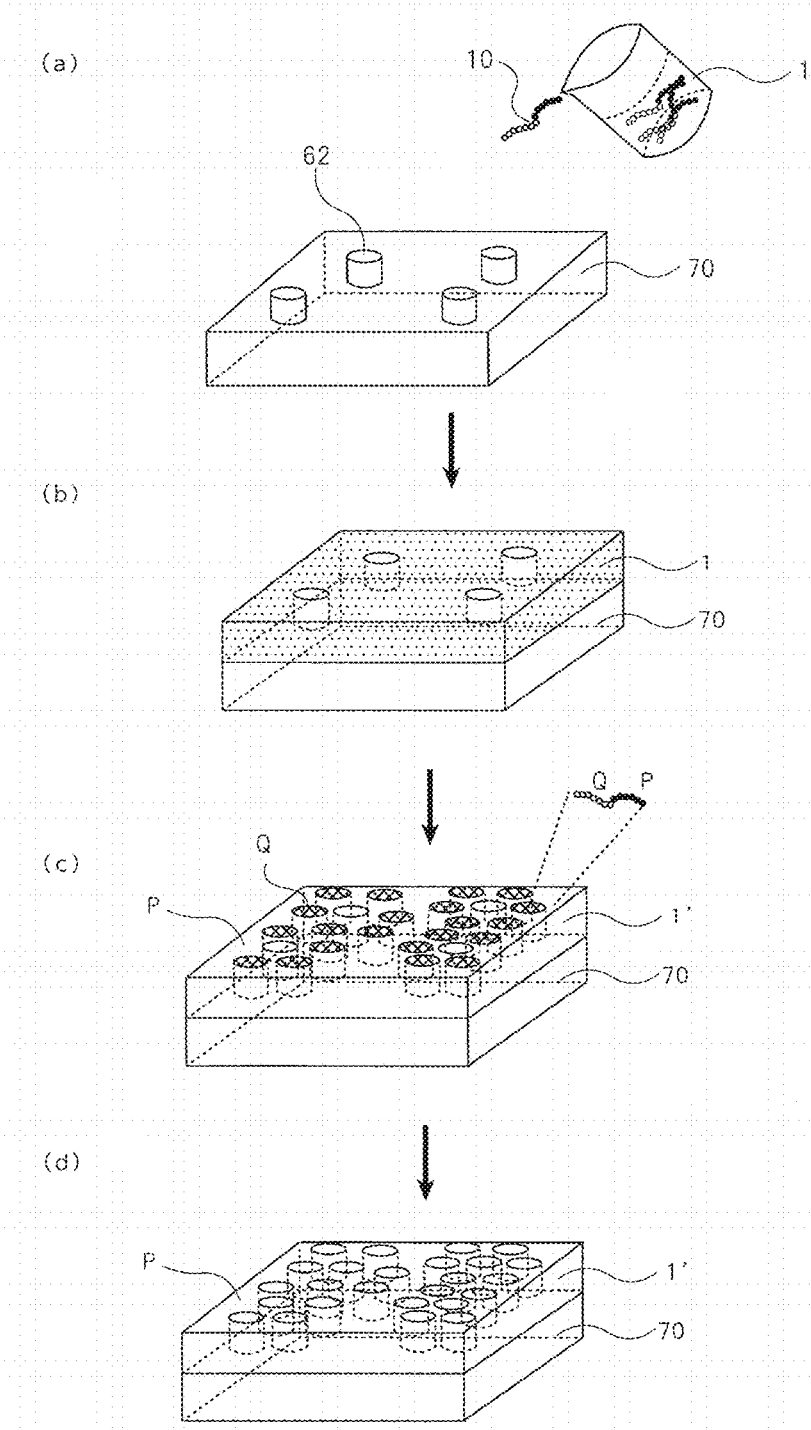
[Figure 3]

[Figure 4]
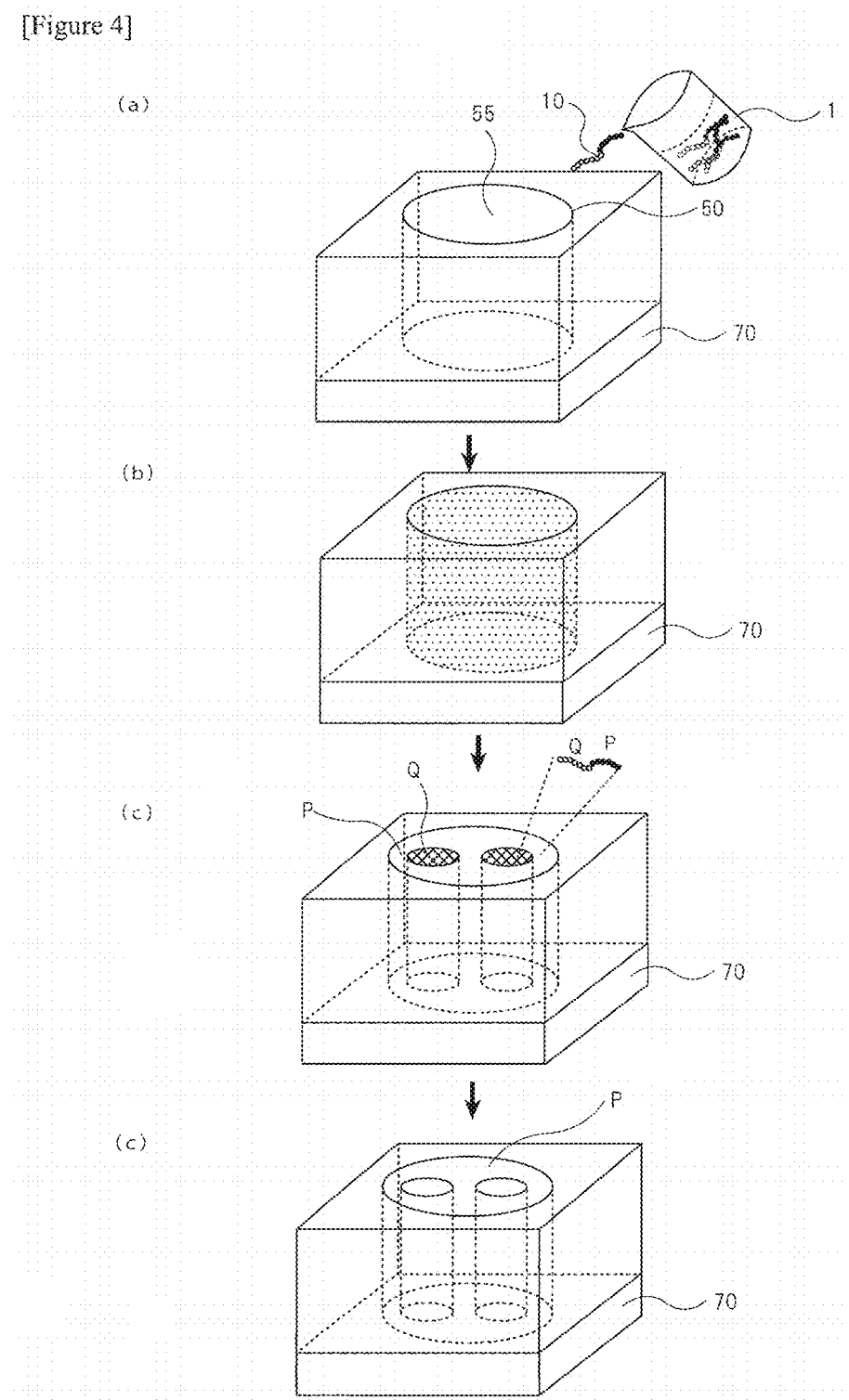

SELF-ASSEMBLY COMPOSITION FOR PATTERN FORMATION AND PATTERN FORMING METHOD

TECHNICAL FIELD

The present invention relates to a self-assembly composition for pattern formation and a pattern forming method.

BACKGROUND ART

Electronic devices such as semiconductors have been required to be highly integrated as a result of miniaturization thereof. With regard to the patterns of semiconductors, miniaturization and the diversification of the shapes have been studied. As such pattern forming methods, a double patterning method, a lithography method using electron beam, and a pattern forming method involving self-assembly using a directed self-assembly material (hereafter also referred to as a "self-assembly composition for pattern formation") have been known.

Since the self-assembly composition for pattern formation undergoes phase separation for self-assembly, it does not need an expensive electron beam drawing device and does not cause complicated patterning processes found in the double patterning method. Accordingly, the self-assembly composition for pattern formation is advantageous in terms of costs. As such self-assembly compositions for pattern formation, for example, diblock copolymers such as polystyrene-polymethyl methacrylate (PS-PMMA) have been known (for example, Non-Patent Document 1). In Non-Patent Document 1, PS-PMMA is applied onto a guide pattern, and is then heated to form a phase-separated structure. Thereafter, an etching step is performed, so that a region consisting of a polymerization unit on one side of the diblock copolymer is removed, thereby forming a fine pattern.

As such a self-assembly composition for pattern formation, the use of a material other than PS-PMMA has also been studied. For example, Patent Document 1 discloses a self-assembly composition for pattern formation, which comprises, as a main chain, a styrene-based polymer, an acryl-based polymer or the like, and has a group containing a heteroatom at the terminus thereof. In Patent Document 1, formation of a sufficiently fine pattern by using a self-assembly composition for pattern formation as described above has been studied.

PRIOR ART DOCUMENTS

Patent Documents

Patent Document 1: JP-A-2014-5325

Non-Patent Documents

Non-Patent Document 1: Toshiba Review Vol. 67, No. 4, 2012, pp. 44-47

SUMMARY OF INVENTION

Object to be Solved by the Invention

PS-PMMA has been frequently used as a self-assembly composition that forms a pattern by phase separation. Although PS-PMMA is a material excellent in forming a pattern with a size of smaller than 30 nm, it has been problematic in that it is difficult for PS-PMMA to control the degree of polymerization upon formation of a pattern with a size of 30 nm or more. In addition, PS-PMMA has also been problematic in that a favorable phase-separated structure cannot be formed due to the limitation of the phase separation ability of the material itself, or in that an extremely long annealing time (heating time) is required to form a phase-separated structure.

Moreover, it has been considered that a sufficiently fine pattern can be formed when such a self-assembly composition for pattern formation as described in Patent Document 1 is used. However, it is necessary to prepare and improve a under layer for carrying out phase separation, and thus, time and effort have been required, for example, upon formation of a fine pattern structure with a size of 10 nm or less. Furthermore, as a result of the studies conducted by the present inventors, it has been revealed that the use of a self-assembly composition for pattern formation as described in Patent Document 1 causes a narrow range of applicable pattern size, and thus that a favorable phase-separated structure cannot be formed, in particular, upon formation of a pattern with a size of 30 nm or more.

Hence, in order to solve the aforementioned problems of prior art techniques, the present inventors have conducted studies for the purpose of providing a self-assembly composition for pattern formation that enables a wide range of applicable pattern size and is capable of easily forming a favorable phase-separated structure.

Means for Solving the Object

As a result of intensive studies conducted directed towards achieving the aforementioned objects, the present inventors have found that a self-assembly composition for pattern formation that enables a wide range of applicable pattern size and is capable of easily forming a favorable phase-separated structure can be formed by allowing a self-assembly composition for pattern formation to comprise a block copolymer comprising at least two polymerization units having predetermined structures.

Specifically, the present invention has the following configurations.

[1] A self-assembly composition for pattern formation, which comprises a block copolymer comprising a polymerization unit (a) having at least one selected from a structure represented by the following formula (103) and a structure represented by the following formula (104), and a polymerization unit (b) having a structure represented by the following formula (105), wherein the content rate of a sugar moiety in the block copolymer is 3% by mass or more and 80% by mass or less based on the total mass of the block copolymer:

[Formula 1]

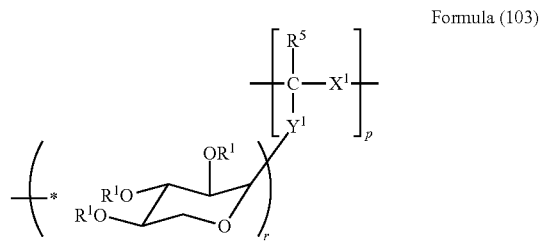

Formula (103)

[Formula 2]

Formula (104)

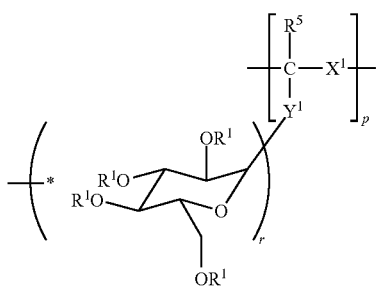

[Formula 3]

Formula (105)

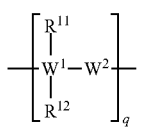

wherein, in the formulae (103) and (104), $R^1$ each independently represents a hydrogen atom, a fluorine atom, a chlorine atom, a bromine atom, an iodine atom, an alkyl group, an acyl group, an aryl group, or a phosphoryl group, and a plurality of $R^1$ may be identical to or different from one another; $R^5$ represents a hydrogen atom or an alkyl group, and a plurality of $R^5$ may be identical to or different from one another, $X^1$ and $Y^1$ each independently represent a single bond or a linking group, a plurality of $X^1$ may be identical to or different from one another, and a plurality of $Y^1$ may be identical to or different from one another; p represents an integer of 2 or more and 1500 or less, r represents an integer of 0 or more, and at least one of a plurality of r represents an integer of 1 or more; and the symbol * represents a binding site with any one of $R^1$, when r represents 2 or more, or represents a binding site with any one oxygen atom to which $R^1$ binds, instead of $R^1$; and in the formula (105), $W^1$ represents a carbon atom or a silicon atom, and a plurality of $W^1$ may be identical to or different from one another; $W^2$ represents —$CR_2$—, —O—, —S—, or —$SiR_2$— (provided that R represents a hydrogen atom or an alkyl group containing 1 to 5 carbon atoms, and a plurality of R may be identical to or different from one another), and a plurality of $W^2$ may be identical to or different from one another; $R^{11}$ represents a hydrogen atom, a methyl group, or a hydroxyl group, and a plurality of $R^{11}$ may be identical to or different from one another; $R^{12}$ represents a hydrogen atom, a hydroxyl group, an acetyl group, a methoxycarbonyl group, an aryl group, or a pyridyl group, and a plurality of $R^{12}$ may be identical to or different from one another; and q represents an integer of 2 or more and 3000 or less.

[2] The self-assembly composition for pattern formation according to [1], wherein the solubility of the block copolymer in at least one selected from propylene glycol monomethyl ether acetate (PGMEA) and dimethylformamide (DMF) is 0.8% by mass or more.

[3] The self-assembly composition for pattern formation according to [1] or [2], wherein the r represents an integer of 0 or more, and at least one of a plurality of r represents an integer of 1 or more and 10 or less.

[4] The self-assembly composition for pattern formation according to any one of [1] to [3], wherein the $R^{12}$ represents a phenyl group.

[5] The self-assembly composition for pattern formation according to any one of [1] to [4], which further comprises an organic solvent.

[6] The self-assembly composition for pattern formation according to any one of [1] to [5], which further comprises an ionic liquid.

[7] A pattern forming method, comprising
applying the self-assembly composition for pattern formation according to any one of [1] to [6] onto a substrate, so as to form a self-assembly film according to self-assembly phase separation, and
subjecting to etching.

[8] The pattern forming method according to [7], wherein the etching is a dry etching.

[9] The pattern forming method according to [7] or [8], which further comprises forming a guide pattern on the substrate before forming the self-assembly film.

Advantageous Effects of Invention

According to the present invention, a self-assembly composition for pattern formation that enables a wide range of applicable pattern size and is capable of easily forming a favorable phase-separated structure can be obtained. The self-assembly composition for pattern formation of the present invention is a material suitable for formation of patterns of all sizes. In addition, by using the self-assembly composition for pattern formation of the present invention, a simple process can be adopted in the case of forming a pattern structure.

BRIEF DESCRIPTION OF DRAWINGS

FIG. 1 is a schematic view showing a pattern-forming step.
FIG. 2 is a schematic view showing a pattern-forming step.
FIG. 3 is a schematic view showing a pattern-forming step.
FIG. 4 is a schematic view showing a pattern-forming step.

EMBODIMENTS OF CARRYING OUT THE INVENTION

Hereinafter, the present invention will be described in detail. The below-mentioned constituent features will be explained based on representative embodiments or specific examples in some cases. However, the present invention is not limited to such embodiments. It is to be noted that substituents, regarding which substitution and/or non-substitution are not explicitly mentioned, are understood that they may optionally have any given substituents.

(Self-Assembly Composition for Pattern Formation)

The present invention relates to a self-assembly composition for pattern formation, which comprises a block copolymer comprising a polymerization unit (a) having at least one selected from a structure represented by the following formula (103) and a structure represented by the following formula (104), and a polymerization unit (b) having a structure represented by the following formula (105). In the present self-assembly composition for pattern formation, the content rate of a sugar moiety in the block copolymer is 3% by mass or more and 80% by mass or less based on the total mass of the block copolymer.

[Formula 4]

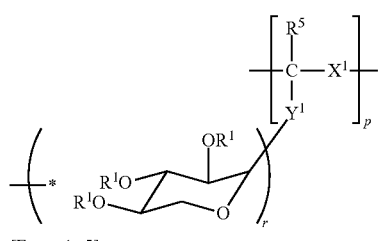

Formula (103)

[Formula 5]

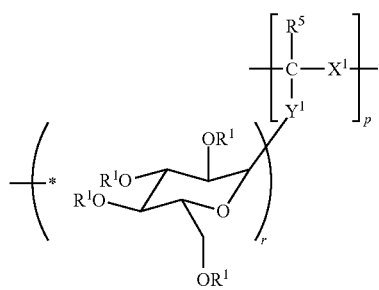

Formula (104)

[Formula 6]

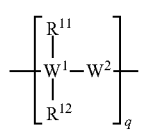

Formula (105)

In the formulae (103) and (104), $R^1$ each independently represents a hydrogen atom, a fluorine atom, a chlorine atom, a bromine atom, an iodine atom, an alkyl group, an acyl group, an aryl group, or a phosphoryl group, and a plurality of $R^1$ may be identical to or different from one another. $R^5$ represents a hydrogen atom or an alkyl group, and a plurality of $R^5$ may be identical to or different from one another. $X^1$ and $Y^1$ each independently represent a single bond or a linking group, a plurality of $X^1$ may be identical to or different from one another, and a plurality of $Y^1$ may be identical to or different from one another. p represents an integer of 2 or more and 1500 or less, r represents an integer of 0 or more, and at least one of a plurality of r represents an integer of 1 or more. The symbol * represents a binding site with any one of $R^1$, when r represents 2 or more, or represents a binding site with any one oxygen atom to which $R^1$ binds, instead of $R^1$.

In the formula (105), $W^1$ represents a carbon atom or a silicon atom, and a plurality of $W^1$ may be identical to or different from one another. $W^2$ represents —$CR_2$—, —O—, —S—, or —$SiR_2$— (provided that R represents a hydrogen atom or an alkyl group containing 1 to 5 carbon atoms, and a plurality of R may be identical to or different from one another), and a plurality of $W^2$ may be identical to or different from one another. $R^{11}$ represents a hydrogen atom, a methyl group, or a hydroxyl group, and a plurality of $R^{11}$ may be identical to or different from one another. $R^{12}$ represents a hydrogen atom, a hydroxyl group, an acetyl group, a methoxycarbonyl group, an aryl group, or a pyridyl group, and a plurality of $R^{12}$ may be identical to or different from one another. q represents an integer of 2 or more and 3000 or less.

The term "self-assembly (Directed self-assembly)" is used in the present description to mean a phenomenon, which is not caused by only control by external factors, but spontaneously constructs formation or structures. In the present invention, a self-assembly composition for pattern formation is applied onto, for example, a substrate, and annealing and the like are then carried out, so that a film having a phase-separated structure (a self-assembly film) can be formed by self-assembling, and thereafter, a part of phase is removed from this self-assembly film, so that a pattern can be formed.

Since the self-assembly composition for pattern formation of the present invention has the above-described configuration, the introduction rate of a sugar moiety (sugar chain) and the introduction rate of the polymerization unit (a) in the block copolymer can be enhanced, and the cohesiveness of each polymerization unit can be thereby enhanced. If the cohesiveness of each polymerization unit is high, the phase separation ability of the block copolymer is increased, and the range of applicable pattern size can also be widened. Moreover, since it becomes easy to control the polymerization degree of the block copolymer in the self-assembly composition for pattern formation of the present invention, even in a case where a large-size pattern is to be formed, a favorable phase-separated structure can be formed. Furthermore, when the self-assembly composition for pattern formation of the present invention is used, the formation of a under layer, etc. is not essential even in a case where a fine pattern structure with a size of, for example, 10 nm or less is to be formed, and thus, the pattern can be formed by a simple process. Further, by enhancing the phase separation ability of the block copolymer, a variation in phase separation interfaces becomes small, and the roughness (unevenness) at the edge, after the removal of one surface, can be reduced.

In the present invention, since there is a large difference in terms of hydrophilicity (hydrophobicity) between the polymerization unit (a) and the polymerization unit (b) and further, the cohesiveness of each polymerization unit is high, phase separation performance is high. Specifically, since the polymerization unit (a) has high hydrophilicity and the polymerization unit (b) has high hydrophobicity, all sizes of patterns can be formed. In addition, in the present invention, the cohesiveness of each polymerization unit can be enhanced by setting the introduction rate of a sugar chain capable of exhibiting the hydrophilicity of the polymerization unit (a) within a suitable range, and as a result, a better phase-separated structure can be easily formed. As such, the self-assembly composition for pattern formation of the present invention is a material suitable for formation of all sizes of patterns. It is to be noted that, in the present description, the size of a pattern is a pitch size corresponding to each component in a phase-separated structure. Specifically, the pitch size of a portion consisting of polymerization units that remain after completion of the etching step is referred to as a pattern size.

The self-assembly composition for pattern formation of the present invention is also characterized in that it has a large difference in the etching rate after formation of a phase-separated structure. Specifically, the etching rate of a region consisting of the polymerization unit (a) having the structure represented by the formula (103) and/or the formula (104) is high, whereas the etching rate of a region consisting of the polymerization unit (b) having the structure represented by the formula (105) is low, and thus, the etching step can be efficiently carried out. Furthermore, the pattern shape after completion of the etching can be easily processed into a desired shape.

(Block Copolymer)

A block copolymer comprises a polymerization unit (a) and a polymerization unit (b). The polymerization unit (a) has at least one selected from the structure represented by the following formula (103) and the structure represented by the following formula (104), whereas the polymerization unit (b) has the structure represented by the following formula (105). The block copolymer is preferably an A-B type diblock copolymer comprising the polymerization unit (a) and the polymerization unit (b), but it may also be a block copolymer comprising a plurality of polymerization units (a) and a plurality of polymerization units (b).

[Formula 7]

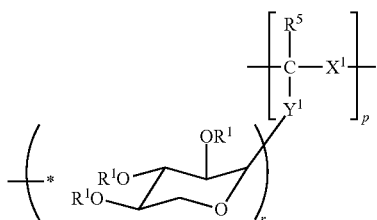

Formula (103)

[Formula 8]

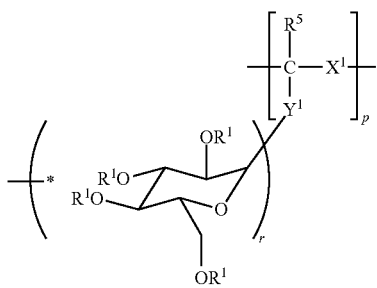

Formula (104)

[Formula 9]

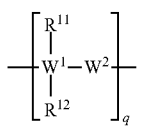

Formula (105)

In the formulae (103) and (104), $R^1$ each independently represents a hydrogen atom, a fluorine atom, a chlorine atom, a bromine atom, an iodine atom, an alkyl group, an acyl group, an aryl group, or a phosphoryl group, and a plurality of $R^1$ may be identical to or different from one another. $R^5$ represents a hydrogen atom or an alkyl group, and a plurality of $R^5$ may be identical to or different from one another. $X^1$ and $Y^1$ each independently represent a single bond or a linking group, a plurality of $X^1$ may be identical to or different from one another, and a plurality of $Y^1$ may be identical to or different from one another. p represents an integer of 2 or more and 1500 or less, r represents an integer of 0 or more, and at least one of a plurality of r represents an integer of 1 or more. The symbol * represents a binding site with any one of $R^1$, when r represents 2 or more, or represents a binding site with any one oxygen atom to which $R^1$ binds, instead of $R^1$.

In the formula (105), $W^1$ represents a carbon atom or a silicon atom, and a plurality of $W^1$ may be identical to or different from one another. $W^2$ represents —$CR_2$—, —O—, —S—, or —$SiR_2$— (provided that R represents a hydrogen atom or an alkyl group containing 1 to 5 carbon atoms, and a plurality of R may be identical to or different from one another), and a plurality of $W^2$ may be identical to or different from one another. $R^{11}$ represents a hydrogen atom, a methyl group, or a hydroxyl group, and a plurality of $R^{11}$ may be identical to or different from one another. $R^{12}$ represents a hydrogen atom, a hydroxyl group, an acetyl group, a methoxycarbonyl group, an aryl group, or a pyridyl group, and a plurality of $R^{12}$ may be identical to or different from one another. q represents an integer of 2 or more and 3000 or less.

In the formulae (103) and (104), $R^1$ each independently represents a hydrogen atom, a fluorine atom, a chlorine atom, a bromine atom, an iodine atom, an alkyl group, an acyl group, an aryl group, or a phosphoryl group, and a plurality of $R^1$ may be identical to or different from one another. Among others, preferably, $R^1$ each independently represents a hydrogen atom or an acyl group containing 1 or more and 3 or less carbon atoms. Besides, the above-described alkyl group also comprises a sugar chain. That is to say, the sugar chain portion of the polymerization unit (a) may further have a branched chain.

When $R^1$ is an alkyl group or an acyl group, the number of carbon atoms possessed by the group can be selected, as appropriate, depending on purpose. For example, the number of carbon atoms is preferably 2 or more, and is also preferably 200 or less, more preferably 100 or less, further preferably 20 or less, and particularly preferably 4 or less.

Specific examples of $R^1$ include: acyl groups such as an acetyl group, a propanoyl group, a butyryl group, an isobutyryl group, a valeryl group, an isovaleryl group, a pivaloyl group, a hexanoyl group, an octanoyl group, a chloroacetyl group, a trifluoroacetyl group, a cyclopentanecarbonyl group, a cyclohexanecarbonyl group, a benzoyl group, a methoxybenzoyl group, or a chlorobenzoyl group; and alkyl groups such as a methyl group, an ethyl group, a propyl group, a butyl group, or a t-butyl group. Among these examples, an acetyl group, a propanoyl group, a butyryl group, and an isobutyryl group are preferable, and an acetyl group is particularly preferable.

In the formulae (103) and (104), $R^5$ represents a hydrogen atom or an alkyl group, and a plurality of $R^5$ may be identical to or different from one another. Among others, $R^5$ is preferably a hydrogen atom or an alkyl group containing 1 or more and 3 or less carbon atoms, and is particularly preferably a hydrogen atom or a methyl group.

In the formulae (103) and (104), $X^1$ and $Y^1$ each independently represent a single bond or a linking group, and a plurality of $X^1$ may be identical to or different from one another, and a plurality of $Y^1$ may be identical to or different from one another.

When $X^1$ is a linking group, examples of the $X^1$ include an alkylene group, —O—, —$NH_2$—, and a group containing a carbonyl group and the like. $X^r$ is preferably a single bond or an alkylene group containing 1 or more and 6 or less carbon atoms, and is more preferably an alkylene group containing 1 or more and 3 or less carbon atoms.

When $Y^1$ is a linking group, examples of the $Y^1$ include an alkylene group, a phenylene group, —O—, and —C(=O)O—. $Y^1$ may also be a linking group formed by combining these groups. Among others, $Y^1$ is preferably a linking group represented by any of the following structural formulae.

[Formula 10]

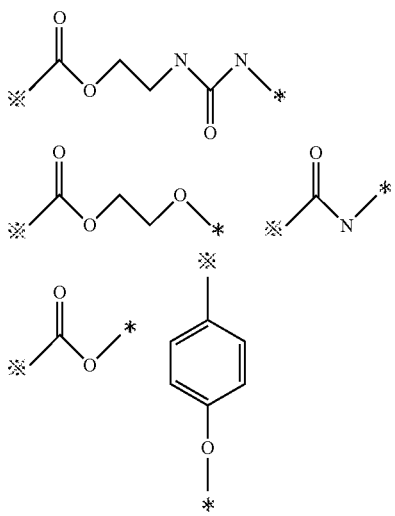

In the above structural formulae, the ⋇ symbol X represents a binding site with the main chain side, and the symbol * represents a binding site with the sugar moiety of the side chain.

In the formulae (103) and (104), p may be 2 or more, preferably 3 or more, more preferably 4 or more, and further preferably 5 or more. On the other hand, p may be 3000 or less, preferably 2500 or less, more preferably 2000 or less, and further preferably 1500 or less.

The value of p in the formulae (103) and (104) is preferably calculated from the value measured by gel permeation chromatography. Other measurement methods include size exclusion chromatography, a light scattering method, a viscosity method, an end-group analysis method, and a sedimentation velocity method. The molecular weight is obtained from such a measurement value, and the obtained molecular weight is then divided by the molecular weight of a unit structure to obtain the p value. At this time, the molecular weight of a unit structure can be obtained from the spectra of $^1$H-NMR and $^{13}$C-NMR and the mean value of r. Moreover, it is more preferable to obtain a unit structure, using information regarding MS spectrum, IR spectrum and the like, as well as the information of NMR.

In the formulae (103) and (104), r represents an integer of 0 or more, and at least one of a plurality of r represents an integer of 1 or more. At least one of r is preferably 2 or more, more preferably 3 or more, and further preferably 5 or more. On the other hand, r is preferably 1500 or less, more preferably 1200 or less, further preferably 500 or less, still further preferably 100 or less, particularly preferably 50 or less, and most preferably 10 or less. Among others, r is preferably an integer of 1 or more and 10 or less.

As is clear from the structural formulae, namely, from the formulae (103) and (104), these structures comprise a glucose unit or a xylose unit, namely, a sugar moiety. In the formulae (103) and (104), since p is 2 or more, sugar moieties each having a different polymerization degree may be linked to one another via $Y^1$ in a p number of repeating units. That is, r may be a different value in the p number of individual repeating units, as long as the r is within the above-described range.

The average polymerization degree of a sugar unit is the same as the preferred range of the above-described r. It is to be noted that the average polymerization degree of the sugar unit is the number of sugar units that form one sugar moiety. When the sugar moiety has a side chain structure, the number of sugar units constituting the side chain is also included in the average polymerization degree. The average polymerization degree of the above-described sugar unit can be calculated by the following measurement method.

First, a solution containing the polymerization unit (a) is maintained at 50° C., and is centrifuged at 15000 rpm for 15 minutes to remove insoluble matters. Thereafter, the amount of total sugar and the amount of reducing sugar (both relative to xylose) in the supernatant are measured. The amount of total sugar is divided by the amount of reducing sugar to calculate an average polymerization degree. When the above-described measurement method cannot be adopted, gel permeation chromatography, size exclusion chromatography, a light scattering method, a viscosity method, an end-group analysis method, a sedimentation velocity method, a MULDI-TOF-MS method, a structure analysis method involving NMR, etc. may be adopted.

When the average polymerization degree of the sugar unit is measured after the synthesis of a block copolymer, the integrated value of a sugar chain-derived peak (around 3.3-5.5 ppm) and the integrated value of other component-derived peak of the polymerization unit (a) are calculated according to $^1$H-NMR, and the average polymerization degree is then calculated based on the ratio of individual integrated values. In addition, when $R^1$ is not a hydrogen atom in the formulae (103) and (104), the integrated value of an —$OR^1$ group-derived peak can also be used, instead of the integrated value of the sugar chain-derived peak (however, in this case, $R^1$ in the —$OR^1$ group is not a sugar chain).

In the formulae (103) and (104), the symbol * represents a binding site with any one of $R^1$, when r represents 2 or more, or represents a binding site with any one oxygen atom to which $R^1$ binds, instead of $R^1$. That is to say, the polymerization portion of sugar units in the formulae (103) and (104) may be either $R^1$ or an oxygen atom to which $R^1$ binds, and either one portion is preferably the polymerization portion. When $R^1$ is an alkyl group having a substituent, $R^1$ may be a sugar chain. Accordingly, even if there is only one binding site represented by the symbol * in the formulae (103) and (104), the sugar chain actually has a side chain consisting of further sugar chains in some cases.

In the formula (105), $W^1$ represents a carbon atom or a silicon atom, and a plurality of $W^1$ may be identical to or different from one another. Among others, $W^1$ is preferably a carbon atom. Moreover, in the formula (105), $W^2$ represents —$CR_2$—, —O—, —S—, or —$SiR_2$— (provided that R represents a hydrogen atom or an alkyl group containing 1 to 5 carbon atoms, and a plurality of R may be identical to or different from one another), and a plurality of $W^2$ may be identical to or different from one another. Among others, $W^2$ is preferably —$CR_2$—, and more preferably —$CH_2$—.

In the formula (105), $R^{11}$ represents a hydrogen atom, a methyl group, or a hydroxyl group, and a plurality of $R^{11}$ may be identical to or different from one another. $R^{11}$ is more preferably a hydrogen atom or a methyl group, and further preferably a hydrogen atom. Moreover, in the formula (105), $R^{12}$ represents a hydrogen atom, a hydroxyl group, an acetyl group, a methoxycarbonyl group, an aryl group, or a pyridyl group, and a plurality of $R^{12}$ may be identical to or different from one another. $R^{12}$ is preferably an aryl group or a pyridyl group, more preferably an aryl group, and further preferably a phenyl group. Furthermore, the phenyl group is preferably a phenyl group having a substituent. Examples of such a phenyl group having a substituent include a 4-t-butylphenyl group, a methoxyphenyl group, a dimethoxyphenyl group, a trimethoxyphenyl group, a trimethylsilylphenyl group, and a tetramethyldisilylphenyl group. Also, $R^{12}$ is preferably a naphthalene group.

As mentioned above, $R^{12}$ is preferably a phenyl group, and the polymerization unit (b) is particularly preferably a styrenic polymer. Examples of an aromatic ring-containing unit other than the styrenic polymer include the following. The styrenic polymer is a polymer obtained by polymerizing a monomeric compound comprising a styrene compound. Examples of the styrene compound include styrene, o-methylstyrene, p-methylstyrene, ethylstyrene, p-methoxystyrene, p-phenylstyrene, 2,4-dimethylstyrene, p-n-octylstyrene, p-n-decylstyrene, p-n-dodecylstyrene, chlorostyrene, bromostyrene, trimethylsilylstyrene, hydroxystyrene, 3,4,5-methoxystyrene, and pentamethyldisilylstyrene. Among others, the styrene compound is preferably at least one selected from styrene and trimethylsilylstyrene, and more preferably styrene. That is to say, the styrenic polymer is preferably at least one selected from polystyrene and polytrimethylsilylstyrene, and is more preferably polystyrene.

In the formula (105), q is preferably 2 or more, more preferably 3 or more, and further preferably 4 or more. On the other hand, q is preferably 3000 or less, more preferably 2000 or less, and further preferably 1500 or less. The value of q in the formula (105) is preferably calculated from the value measured by gel permeation chromatography. Other measurement methods include size exclusion chromatography, a light scattering method, a viscosity method, an end-group analysis method, and a sedimentation velocity method. The molecular weight is obtained from such a measurement value, and the obtained molecular weight is then divided by the molecular weight of a unit structure to obtain the q value. At this time, the molecular weight of a unit structure can be obtained from the spectra of $^1$H-NMR. Moreover, it is more preferable to obtain a unit structure, using information regarding MS spectrum, IR spectrum and the like, as well as the information of NMR.

The polymerization unit (a) comprises at least one selected from the structure represented by the above formula (103) and the structure represented by the above formula (104). Preferably, the polymerization unit (a) mainly comprises the structure represented by the above formula (103). This is considered because the structure represented by the above formula (103) is more compact than the structure represented by the above formula (104) and thus, it becomes easy to control phase separation by the structure represented by the above formula (103).

The weight average molecular weight (Mw) of the block copolymer is preferably 500 or more, more preferably 1000 or more, and further preferably 1500 or more. On the other hand, the weight average molecular weight (Mw) of the block copolymer is preferably 1,000,000 or less, more preferably 500,000 or less, further preferably 300,000 or less, and still further preferably 250,000 or less. By setting the weight average molecular weight (Mw) of the block copolymer within the above-described range, a favorable phase-separated structure can be formed even in a case where a large-size pattern is to be formed. In addition, even in a case where a fine pattern structure is to be formed, such a pattern can be formed by a simple process. It is to be noted that the weight average molecular weight (Mw) of the block copolymer is a value measured relative to polystyrene according to GPC.

The ratio (Mw/Mn) between the weight average molecular weight (Mw) and the number average molecular weight (Mn) of the block copolymer is preferably 1 or more. On the other hand, the ratio Mw/Mn is preferably 2 or less, more preferably 1.5 or less, and further preferably 1.3 or less. By setting the ratio Mw/Mn within the above-described range, the self-assembly composition for pattern formation of the present invention can form a fine, good pattern structure with higher accuracy.

The solubility of the block copolymer in at least one selected from propylene glycol monomethyl ether acetate (PGMEA) and dimethylformamide (DMF) is preferably 0.8% by mass or more, more preferably 0.9% by mass or more, and further preferably 1.0% by mass or more. The upper limit value of the solubility of the block copolymer in the above-described solvents is not particularly limited, and it can be set, for example, at 20% by mass. It is to be noted that the above-described solubility is solubility in, at least, either PGMEA or DMF, and the block copolymer used in the present invention preferably has solubility in either one of the above-described solvents that is a predetermined value or more.

With regard to the method of measuring the solubility of the block copolymer, while PGMEA or DMF is gradually added to a predetermined amount of block copolymer, it is stirred, so that the block copolymer is dissolved in the solvent. The amount of the solvent at the time of dissolving the block copolymer therein is recorded. For stirring, a magnetic stirrer or the like may be used. The solubility is calculated according to the following equation:

Solubility (%)=mass of block copolymer/amount of solvent at time of dissolution×100

Besides, the liquid temperature of the solvent is set at 25° C., and dissolution of the block copolymer is confirmed by visually observing that the solution has become transparent.

The solubility of the block copolymer in, at least, either PGMEA or DMF, which is within the above-described range, means that the polymerization degree of a sugar-derived unit constituting the sugar moiety in the formula (103) and/or the formula (104) is a predetermined value or less. Specifically, the value of r in the formula (103) and/or the formula (104) is preferably in a predetermined range or less. Thus, by controlling the polymerization degree of the sugar moiety in the formula (103) and/or the formula (104), the solubility of the block copolymer in a solvent can be enhanced, and a self-assembly composition for pattern formation having excellent phase separation ability can be obtained. Moreover, by controlling the polymerization degree of the sugar-derived unit in the formula (103) and/or the formula (104), the content rate of the sugar moiety can be easily enhanced, and thereby, the cohesive power of the polymerization unit (a) in the block copolymer can be effectively enhanced. In the case of using a block copolymer having high cohesive power, the range of applicable pattern size of a self-assembly composition for pattern formation is widened, and also, a self-assembly composition for pattern formation can be easily formed. Furthermore, by controlling the polymerization degree of the sugar-derived unit, it becomes possible to easily synthesize the polymerization unit (a), and consequently, the production efficiency of the block copolymer can also be enhanced.

In order to set the value of r within a predetermined range, a method of controlling the r value by regulating the length of a sugar chain before formation of a block copolymer is preferably adopted. Specifically, the length of a sugar chain is controlled by separation and purification using a silica gel column or an ion exchange resin, separation and purification involving a reverse osmosis membrane, ultrafiltration, etc., a method of cleaving a sugar chain using enzyme, or anti-solvent crystallization from oligosaccharides, so that the r value can be set within a predetermined range. Besides, the length of such a sugar chain can be confirmed, for example, using Shodex Column KS-801. Other than this method, the length of a sugar chain can also be confirmed by MULDI TOF MS, gel permeation chromatography, size exclusion chromatography, a light scattering method, a viscosity method, an end-group analysis method, a sedimentation velocity method, etc.

The content rate of the sugar moiety in the block copolymer is 3% by mass or more and 80% by mass or less based on the total mass of the block copolymer. The content rate of the sugar moiety may be 3% by mass or more, preferably 10% by mass or more, more preferably 15% by mass or more, and further preferably 25% by mass or more. On the other hand, the content rate of the sugar moiety may be 80% by mass or less, preferably 70% by mass or less, and more preferably 60% by mass or less.

Herein, the sugar moiety has a unit represented by the following formula (1) or the following formula (2). The sugar moiety consists of a single sugar-derived unit represented by the following formula (1) or the following formula (2), or is formed by polymerizing two or more sugar-derived units.

[Formula 11]

Formula (1)

[Formula 12]

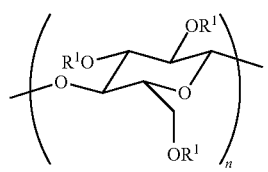

Formula (2)

In the formulae (1) and (2), $R^1$ each independently represents a hydrogen atom, a fluorine atom, a chlorine atom, a bromine atom, an iodine atom, an alkyl group, an acyl group, an aryl group, or a phosphoryl group, and a plurality of $R^1$ may be identical to or different from one another.

The content rate of the sugar moiety in the block copolymer can be calculated by calculating the total mass of the aforementioned sugar-derived unit(s) comprised in the block copolymer, and then dividing the calculated total mass by the total mass of the block copolymer. Specifically, the content rate of the sugar moiety in the block copolymer block copolymer can be calculated according to the following equation:

Content rate of sugar moiety (% by mass)=total mass of sugar-derived unit(s)/weight average molecular weight of block copolymer×100

The total mass of the sugar-derived unit(s) can be obtained, for example, from $^1$H-NMR and the weight average molecular weight of the block copolymer. Specifically, the total mass can be calculated according to the following equation:

Total mass of sugar-derived unit(s)=polymerization degree of sugar-derived unit(s)×molecular weight of sugar That is, the content rate of the sugar moiety can be calculated according to the following equation:

Content rate of sugar moiety (% by mass)=polymerization degree of sugar-derived unit(s)×molecular weight of sugar×number of units with polymerization unit (a)/weight average molecular weight of block copolymer Herein, the number of units with the polymerization unit (a) can be calculated from the weight average molecular weight of the block copolymer, the unit ratio, and the molecular weight of each structural unit.

The block copolymer may comprise a constitutional unit having a mesogenic structure. Examples of the mesogenic structure include the following structures. In the structures, the symbol * represents a linking site.

[Formula 13]

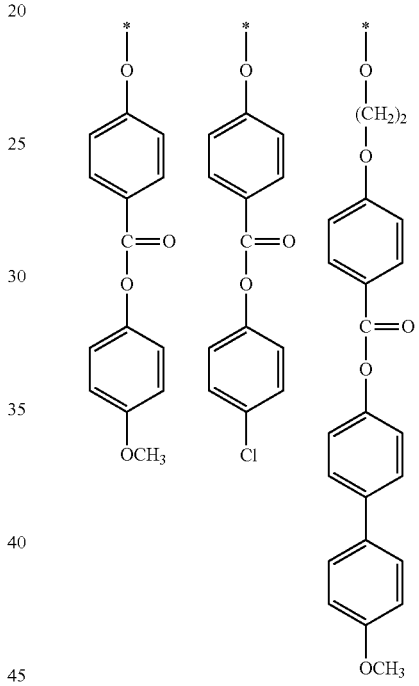

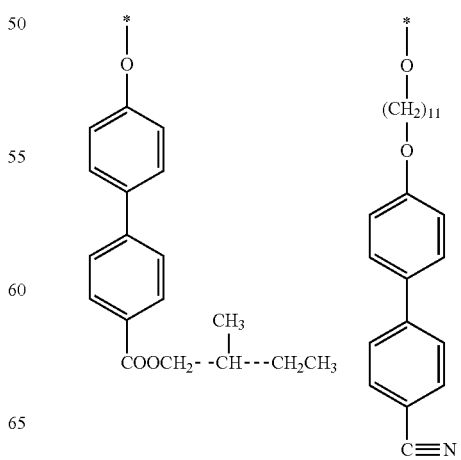

[Formula 14]

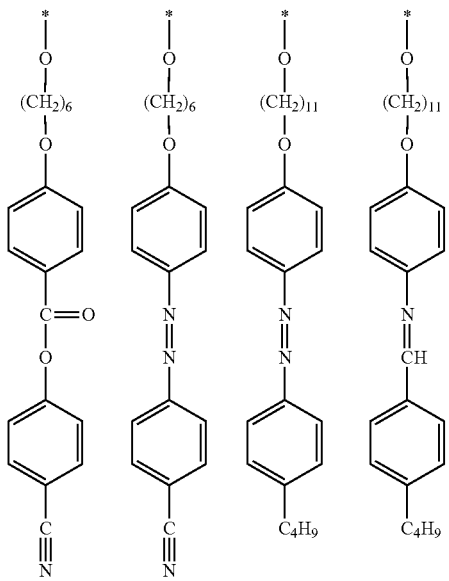

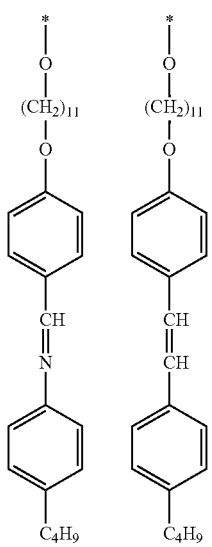

[Formula 15]

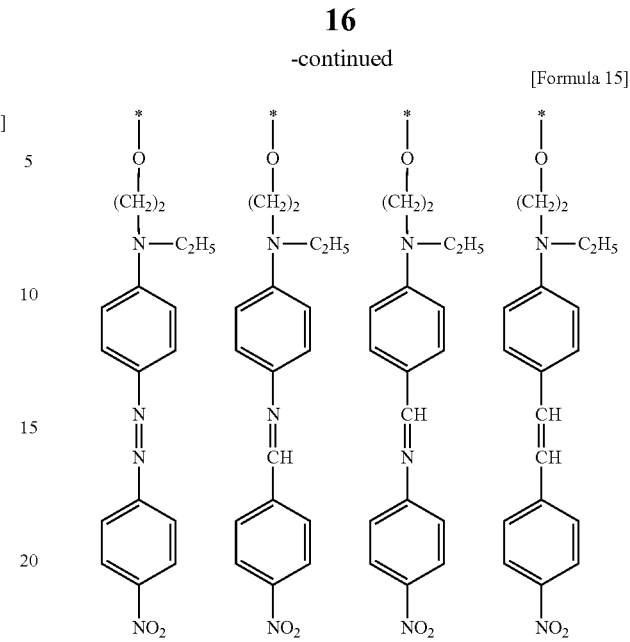

The block copolymer may also be represented by the following formula (113) or the following formula (114).

[Formula 16]

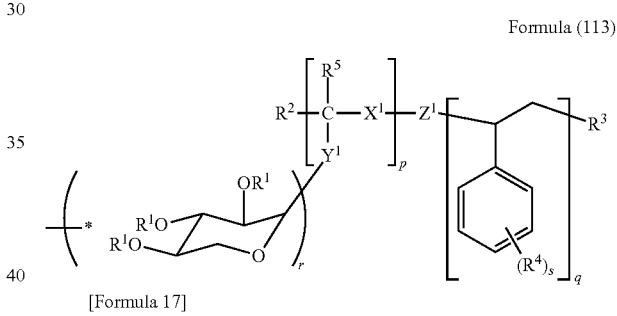

Formula (113)

[Formula 17]

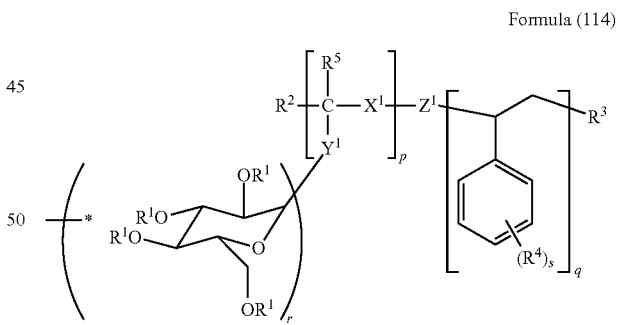

Formula (114)

In the formulae (113) and (114), $R^1$ each independently represent a hydrogen atom, a fluorine atom, a chlorine atom, a bromine atom, an iodine atom, an alkyl group, an acyl group, an aryl group, or a phosphoryl group, and a plurality of $R^1$ may be identical to or different from one another. $R^2$ represents a hydrogen atom or a substituent; $R^3$ represents a hydrogen atom or a substituent; $R^4$ represents a halogen atom, a hydroxyl group, an alkyl group, an acyl group, a trimethylsilyl group, or a 1,1,2,2,2-pentamethyldisilyl group, wherein when s is 2 or more, a plurality of $R^4$ may be identical to or different from one another. $R^5$ represents a hydrogen atom or an alkyl group, and a plurality of $R^5$ may be identical to or different from one another. $X^1$, $Y^1$ and $Z^1$ each independently represent a single bond or a linking group, a plurality of $X^1$ may be identical to or different from one another, and a plurality of $Y^1$ may be identical to or different from one another. p represents an integer of 2 or more and 1500 or less, q represents an integer of 2 or more and 3000 or less, r represents an integer of 0 or more, at least one of a plurality of r represents an integer of 1 or more, and s represents an integer of 0 or more and 5 or less. The symbol * represents a binding site with any one of $R^1$, when r represents 2 or more, or represents a binding site with any one oxygen atom to which $R^1$ binds, instead of $R^1$.

The preferred range of $R^1$ in the formulae (113) and (114) is the same as the preferred range of $R^1$ in the formulae (103) and (104).

In the formulae (113) and (114), $R^2$ represents a hydrogen atom or a substituent. Examples of the substituent include: acyl groups such as a fluorine atom, a chlorine atom, a bromine atom, an iodine atom, an amino group, an acetyl group, a propanoyl group, a butyryl group, an isobutyryl group, a valeryl group, an isovaleryl group, a pivaloyl group, a hexanoyl group, an octanoyl group, a chloroacetyl group, a trifluoroacetyl group, a cyclopentanecarbonyl group, a cyclohexanecarbonyl group, a benzoyl group, a methoxybenzoyl group, or a chlorobenzoyl group; and alkyl groups such as a methyl group, an ethyl group, a propyl group, an n-butyl group, a sec-butyl group, or a tert-butyl group. $R^2$ is preferably a hydrogen atom, an acetyl group, a propanoyl group, a butytyl group, an isobutyryl group, an n-butyl group, a sec-butyl group, or a tert-butyl group, and is particularly preferably a hydrogen atom or an acetyl group.

In addition, $R^2$ may also be, for example, a substituent having the structure represented by the aforementioned formula (105), or may further comprise the aforementioned substituent and a substituent(s) having the structure(s) represented by the aforementioned formula (103) and/or formula (104). That is to say, the block copolymer may be a polymer comprising two or more polymerization units (b), or may also be a polymer having a structure of B-A-B type or B-A-B-A type.

In the formulae (113) and (114), $R^3$ represents a hydrogen atom or a substituent. Examples of the substituent include a hydrogen atom, a fluorine atom, a chlorine atom, a bromine atom, an iodine atom, a hydroxyl group, an acetyl group, a propanoyl group, a butyryl group, a methyl group, an ethyl group, a propyl group, a butyl group, a t-butyl group, a trimethylsilyl group, and groups represented by the following structural formulae.

[Formula 18]

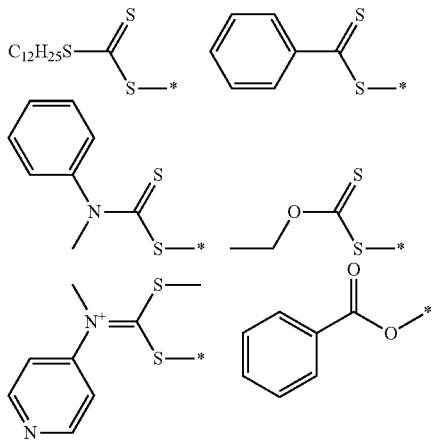

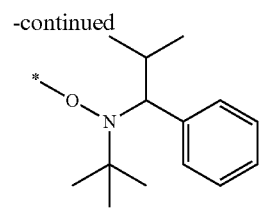

In the above structural formulae, the symbol * represents a binding site with an aromatic ring-containing unit.

In addition, $R^3$ may also be a substituent(s) having the structure(s) represented by the aforementioned formula (103) and/or formula (104), or may further comprise a substituent having the structure represented by the aforementioned formula (105). That is to say, the block copolymer may be a polymer comprising two or more polymerization units (a), or may also be a polymer having a structure of A-B-A type or A-B-A-B type.

In the formulae (113) and (114), $R^4$ represents a halogen atom, a hydroxyl group, an alkyl group, an acyl group, a trimethylsilyl group, or a 1,1,2,2,2-pentamethyldisilyl group. In the formulae, s represents an integer of 0 or more and 5 or less, and s is preferably 0. When s is 2 or more, a plurality of $R^4$ may be identical to or different from one another.

The preferred range of $R^5$ in the formulae (113) and (114) is the same as the preferred range of $R^5$ in the formulae (103) and (104).

In the formulae (113) and (114), $X^1$, $Y'$ and $Z'$ each independently represent a single bond or a linking group, wherein a plurality of $X^1$ may be identical to or different from one another, and a plurality of $Y^1$ may be identical to or different from one another.

$X^1$ and $Y^1$ in the formulae (113) and (114) are each independently the same as the preferred range of $X^1$ and $Y^1$ in the formulae (103) and (104).

When $Z^1$ in the formulae (113) and (114) is a linking group, examples of the linking group include —O—, an alkylene group, a disulfide group, and groups represented by the following structural formulae. When $Z^1$ is an alkylene group, the carbon atoms in the alkylene group may be substituted with heteroatoms. Examples of such a heteroatom include a nitrogen atom, an oxygen atom, a sulfur atom, and a silicon atom. In addition, when $Z^1$ is a linking group, the length of the linking group is preferably shorter than the length of the polymerization unit (a) or the polymerization unit (b).

[Formula 19]

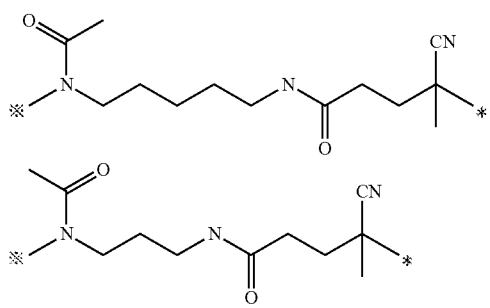

-continued

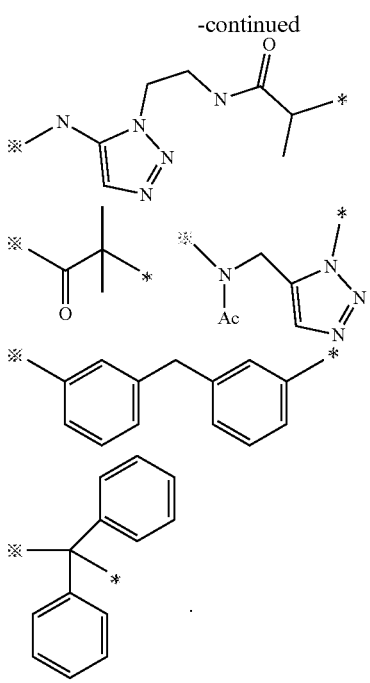

In the above structural formulae, the symbol * represents a binding site with an aromatic ring-containing unit, and the symbol ※ represents a binding site with $X^1$.

In the formulae (113) and (114), p represents an integer of 2 or more and 1500 or less, and q represents an integer of 2 or more and 3000 or less. The preferred ranges of p and q in the formulae (113) and (114) are the same as the preferred ranges of p and q in the formulae (103) to (105), respectively.

In the formulae (113) and (114), r represents an integer of 0 or more, and at least one of a plurality of r represents an integer of 1 or more. The preferred range of r in the formulae (113) and (114) is the same as the preferred range of r in the formulae (103) and (104), respectively.

The unit ratio between the polymerization unit (a) and the polymerization unit (b) in the block copolymer is preferably 1:9 to 9:1, and more preferably 1:9 to 5:5. That is, in the formulae (113) and (114), p:q is preferably 1:9 to 9:1, and more preferably 1:9 to 5:5. Besides, the above-described ratio can be adjusted, as appropriately, depending on the shape of pattern. For example, when the block copolymer forms a lamellar phase-separated structure, the unit ratio between the polymerization unit (a) and the polymerization unit (b) is preferably 3:7 to 7:3. On the other hand, when the block copolymer forms a cylinder-type phase-separated structure having a sugar chain therein, the component ratio between the polymerization unit (a) and the polymerization unit (b) is preferably 2:8 to 5:5. Moreover, when block copolymer forms a cylinder-type phase-separated structure having a sugar chain outside thereof, the component ratio between the polymerization unit (a) and the polymerization unit (b) is preferably 5:5 to 8.5:1.5. It is to be noted that the unit ratio means the ratio between the number of units constituting the polymerization unit (a) and the number of units constituting the polymerization unit (b).

(Organic Solvent)

Preferably, the self-assembly composition for pattern formation of the present invention further comprises an organic solvent. Examples of the organic solvent include an alcohol-based solvent, an ether-based solvent, a ketone-based solvent, a sulfur-based solvent, an amide-based solvent, an ester-based solvent, and a hydrocarbon-based solvent. These solvents may be used alone or in combination of two or more types.

Examples of the alcohol-based solvent include: methanol, ethanol, n-propanol, i-propanol, n-butanol, i-butanol, sec-butanol, tert-butanol, n-pentanol, i-pentanol, 2-methylbutanol, sec-pentanol, tert-pentanol, 3-methoxybutanol, n-hexanol, 2-methylpentanol, sec-hexanol, 2-ethylbutanol, sec-heptanol, 3-heptanol, n-octanol, 2-ethylhexanol, sec-octanol, n-nonyl alcohol, 2,6-dimethyl-4-heptanol, n-decanol, sec-undecyl alcohol, trimethylnonyl alcohol, sec-tetradecyl alcohol, sec-heptadecyl alcohol, furfuryl alcohol, phenol, cyclohexanol, methylcyclohexanol, 3,3,5-trimethyl-cyclohexanol, benzyl alcohol, and diacetone alcohol; and ethylene glycol, 1,2-propylene glycol, 1,3-butylene glycol, 2,4-pentanediol, 2-methyl-2,4-pentanediol, 2,5-hexanediol, 2,4-heptanediol, 2-ethyl-1,3-hexanediol, diethylene glycol, dipropylene glycol, triethylene glycol, tripropylene glycol, 1H, 1H-trifluoroethanol, 1H,1H-pentafluoropropanol, and 6-(perfluoroethyl)hexanol.

Moreover, examples of a partially etherified polyhydric alcohol-based solvent include ethylene glycol monomethyl ether, ethylene glycol monoethyl ether, ethylene glycol monopropyl ether, ethylene glycol monobutyl ether, ethylene glycol monohexyl ether, ethylene glycol monophenyl ether, ethylene glycol mono-2-ethylbutyl ether, diethylene glycol monomethyl ether, diethylene glycol monoethyl ether, diethylene glycol monopropyl ether, diethylene glycol monobutyl ether, diethylene glycol monohexyl ether, diethylene glycol dimethyl ether, diethylene glycol ethylmethyl ether, propylene glycol monomethyl ether (PGME), propylene glycol monoethyl ether, propylene glycol monopropyl ether, propylene glycol monobutyl ether, dipropylene glycol monomethyl ether, dipropylene glycol monoethyl ether, and dipropylene glycol monopropyl ether.

Examples of the ether-based solvent include diethyl ether, dipropyl ether, dibutyl ether, diphenyl ether, and tetrahydrofuran (THF).

Examples of the ketone-based solvent include acetone, methylethyl ketone, methyl-n-propyl ketone, methyl-n-butyl ketone, diethyl ketone, methyl-i-butyl ketone, methyl-n-pentyl ketone, ethyl-n-butyl ketone, methyl-n-hexyl ketone, di-i-butyl ketone, trimethylnonanone, cyclopentanone, cyclohexanone, cycloheptanone, cyclooctanone, methylcyclohexanone, 2,4-pentanedione, acetonylacetone, acetophenone and furfural.

The sulfur-based solvent is, for example, dimethyl sulfoxide.

Examples of the amide-based solvent include N,N'-dimethylimidazolidinone, N-methylformamide, N,N-dimethylformamide, N,N-diethylformamide, acetamide, N-methylacetamide, N,N-dimethylacetamide, N-methylpropionamide, and N-methylpyrrolidone.

Examples of the ester-based solvent include diethyl carbonate, propylene carbonate, methyl acetate, ethyl acetate, γ-butyrolactone, γ-valerolactone, n-propyl acetate, i-propyl acetate, n-butyl acetate, i-butyl acetate, sec-butyl acetate, n-pentyl acetate, sec-pentyl acetate, 3-methoxybutyl acetate, methylpentyl acetate, 2-ethylbutyl acetate, 2-ethylhexyl acetate, benzyl acetate, cyclohexyl acetate, methylcyclohexyl acetate, n-nonyl acetate, methyl acetoacetate, ethyl acetoacetate, ethylene glycol monomethyl ether acetate, ethylene glycol monoethyl ether acetate, diethylene glycol monomethyl ether acetate, diethylene glycol monoethyl ether acetate, diethylene glycol mono-n-butyl ether acetate, propylene glycol monomethyl ether acetate (PGMEA), propylene glycol monoethyl ether acetate, propylene glycol monopropyl ether acetate, propylene glycol monobutyl ether acetate, dipropylene glycol monomethyl ether acetate, dipropylene glycol monoethyl ether acetate, glycol diacetate, methoxytriglycol acetate, ethyl propionate, n-butyl propionate, i-amyl propionate, methyl 3-methoxypropionate, diethyl oxalate, di-n-butyl oxalate, methyl lactate, ethyl lactate, n-butyl lactate, n-amyl lactate, diethyl malonate, dimethyl phthalate, and diethyl phthalate.

Examples of the hydrocarbon-based solvent include: aliphatic hydrocarbon-based solvents such as n-pentane, i-pentane, n-hexane, i-hexane, n-heptane, i-heptane, 2,2,4-trimethylpentane, n-octane, i-octane, cyclohexane, or methylcyclohexane; and aromatic hydrocarbon-based solvents such as benzene, toluene, xylene, mesitylene, ethyl benzene, trimethyl benzene, methylethyl benzene, n-propyl benzene, i-propyl benzene, diethyl benzene, i-butyl benzene, triethyl benzene, di-i-propyl benzene, n-amyl naphthalene, or anisole.

Among these examples, propylene glycol monomethyl ether acetate (PGMEA), N,N-dimethylformamide (DMF), propylene glycol monomethyl ether (PGME), anisole, ethanol, methanol, acetone, methyl ethyl ketone, hexane, tetrahydrofuran (THF), dimethyl sulfoxide (DMSO), 1H,1H-trifluoroethanol, 1H,1H-pentafluoropropanol, 6-(perfluoroethyl)hexanol, ethyl acetate, propyl acetate, butyl acetate, cyclohexanone, and furfural are more preferable, PGMEA or DMF is even more preferable, and PGMEA is further preferable. These solvents may be used alone or in combination of two or more types.

The content of such an organic solvent is preferably 10% by mass or more, more preferably 20% by mass or more, and further preferably 30% by mass or more, based on the total mass of the self-assembly composition for pattern formation. On the other hand, the content of such an organic solvent is preferably 99.9% by mass or less, more preferably 99% by mass or less, and further preferably 98% by mass or less, based on the total mass of the self-assembly composition for pattern formation. By setting the content of the organic solvent within the above-described range, the coating properties of the self-assembly composition can be improved upon formation of a pattern.

(Ionic Liquid)

Preferably, the self-assembly composition for pattern formation of the present invention further comprises an ionic liquid. The ionic liquid means a solvent, which is in the state of liquid at a temperature of 100° C. or lower and is composed of only ions. With regard to ions constituting such an ionic liquid, at least one of a cationic part and an anionic part is composed of organic ions.

By allowing the self-assembly composition for pattern formation to comprise an ionic liquid, compatibility between the block copolymer and the organic solvent can be enhanced. Moreover, the ionic liquid also has a function of promoting the phase separation of the block copolymer.

The ionic liquid consists of a cationic part and an anionic part. The cationic part of the ionic liquid is not particularly limited, and in general, those used in the cationic part of an ionic liquid can be used herein. Preferred examples of the cationic part of the ionic liquid include a nitrogen-containing aromatic ion, an ammonium ion, and a phosphonium ion.

Examples of the nitrogen-containing aromatic cation include a pyridinium ion, a pyridazinium ion, a pyrimidinium ion, a pyrazinium ion, an imidazolium ion, a pyrazonium ion, an oxazolium ion, a 1,2,3-triazolium ion, a 1,2,4-triazolium ion, a thiazolium ion, a piperidinium ion, and a pyrrolidinium ion.

Examples of the anionic portion of the ion liquid include a halogen ion, a carboxylate ion, a phosphinate ion, a phosphate ion, a phosphonate ion, and a bis(trifluoromethylsulfonyl)imide ion, and among these, a bis(trifluoromethylsulfonyl)imide ion is preferable. Examples of the halogen ion include a chloride ion, a bromide ion, and an iodide ion, and among these, a chloride ion is preferable. Examples of the carboxylate ion include a formate ion, an acetate ion, a propionate ion, a butyrate ion, a hexanoate ion, a maleate ion, a fumarate ion, an oxalate ion, a lactate ion, and a pyruvate ion, and among these, a formate ion, an acetate ion, and a propionate ion are preferable.

The content of the ionic liquid is preferably 0.1% by mass or more, more preferably 1% by mass or more, even more preferably 2% by mass or more, and further preferably 3% by mass or more, based on the total mass of the self-assembly composition for pattern formation. On the other hand, the content of the ionic liquid is preferably 99% by mass or less, more preferably 98% by mass or less, and further preferably 97% by mass or less, based on the total mass of the self-assembly composition for pattern formation. By setting the content of the ionic liquid within the above-described range, compatibility between the block copolymer and the organic solvent can be enhanced. Moreover, by setting the content of the ionic liquid within the above-described range, the phase separation of the block copolymer can be promoted.

(Optional Components)

The self-assembly composition for pattern formation of the present invention may further comprise optional components. The optional component is, for example, a surfactant. By allowing the self-assembly composition for pattern formation to comprise a surfactant, the coating properties of the self-assembly composition on a substrate or the like upon pattern formation can be improved. Examples of a preferred surfactant include a nonionic surfactant, a fluorine-based surfactant, and a silicone-based surfactant. These surfactants may be used alone or in combination of two or more types.

The self-assembly composition for pattern formation of the present invention may comprise monomeric components of the block copolymer. For example, in order to improve desired phase separation properties, a monomer constituting the polymerization unit (a) or a monomer constituting the polymerization unit (b) can be added, as appropriate, to the present self-assembly composition for pattern formation.

(Method for Producing Self-Assembly Composition for Pattern Formation)

<Method of Extracting Polymerization Unit (a)>

The polymerization unit (a) may be synthesized, but the synthesis may also be combined with a step of extracting it from lignocellulose or the like derived from woody plants or herbaceous plants. When the sugar moiety of the polymerization unit (a) is extracted from lignocellulose or the like derived from woody plants or herbaceous plants, the extraction method described in JP-A-2012-100546, etc. can be applied.

<Extraction of Xylooligosaccharide>

As a woody plant-derived lignocellulose raw material, the xylem or bark of broadleaf trees or coniferous trees is preferably used, but other sites such as a branch or a leaf can also be used. As a herbaceous plant-derived lignocellulose raw material, the sites of kenaf, hemp, bagasse, rice, etc., such as a stem or a leaf, can be used without any particular limitation. Upon extraction of the polymerization unit (a), it is preferable to use a fibrillated product obtained by performing a fibrillation treatment on the sites of woody plants, such as a xylem or a bark, or the sites of herbaceous plants, such as a stem, a branch or a leaf. After completion of the fibrillation treatment, the obtained product is preferably used in the form of pulp. The pulp used herein is not particularly limited, and examples thereof include chemical pulp, mechanical pulp, and deinked pulp. A broadleaf tree-derived chemical pulp is preferable. Examples of a digestion method for obtaining chemical pulp include known digestion methods such as craft digestion, polysulfide digestion, soda digestion, or alkali sulfite digestion. Taking into consideration the quality of pulp, the energy efficiency for obtaining pulp, etc., it is preferable to use the craft digestion method. In addition, it is more preferable to use pulp that is bleached with oxygen after completion of the craft digestion.

When the polymerization unit (a) is extracted from lignocellulose or the like derived from woody plants or herbaceous plants, pulp slurry is preferably subjected to an enzyme treatment, a reverse osmosis membrane treatment, an ultrafiltration treatment, or an acid treatment, and is more preferably, further subjected to an activated carbon treatment and an ion exchange treatment.

In the enzyme treatment step, a hemicellulase treatment is preferably carried out. The hemicellulase used in the present invention is not particularly limited, as long as it comprises xylanase activity. Examples of the hemicellulase include: commercially available enzyme preparations, such as, as product names, Cartazyme (manufactured by Clariant), Pulpzyme (manufactured by Novo Nordisk), Ecopulp (manufactured by Rohm Enzyme, Inc.), Sumizyme (manufactured by Shin-Nippon Chemical Industrial Co., Ltd.), Multifect Xylanase (manufactured by Genoncor Inc.), or Xylanase Conch (manufactured by Advanced Bio-Chemicals Co., Ltd.); and xylanase produced by microorganisms such as genus *Trichoderma*, genus *Thermomyces*, genus *Aureobasidium*, genus *Streptomyces*, genus *Aspergillus*, genus *Clostridium*, genus *Bacillus*, genus *Thermotoga*, genus *Thermoascus*, genus Caldocellum, or genus Thermomonospora.

In the hemicellulase treatment step, by adjusting the amount of hemicellulase added to pulp and the reaction time, the concentration of oligosaccharide eluted from the pulp and the polymerization degree of oligosaccharide can be controlled. In general, as the added amount of hemicellulase increases, or as the reaction time prolongs, the concentration of oligosaccharide in the reaction solution increases and the polymerization degree of oligosaccharide decreases. Accordingly, in order to stably obtain a high concentration of molasses containing a high polymerization degree of oligosaccharide, it is preferable that a suitable amount of hemicellulase (i.e., hemicellulase in which low-molecular-weight hemicellulase is not decomposed) be added to pulp, and that an aliquot of the molasses after completion of the reaction be returned to an enzyme reaction tank and be subjected to an enzyme reaction again. Thereby, while maintaining a high polymerization degree of oligosaccharide, the sugar concentration in the high polymerization degree of oligosaccharide can be enhanced as the time lapses.

Besides, the suitable amount of hemicellulase added to pulp and the reaction time are different depending on the type of the used enzyme. For example, in the case of multifect xylanase, the reaction time is preferable 10 minutes or longer and 240 minutes or shorter. In addition, the amount of hemicellulase added to pulp is preferably 2 units/g or more and 200 units/g or less, based on the absolute dry mass of the pulp.

The polymerization degree of oligosaccharide, which is eluted in the reaction solution obtained by subjecting pulp to a hemicellulase treatment, is fluctuated depending on the type of the used enzyme or reaction conditions. For example, in the case of using multifect xylanase, under conditions of a pulp concentration of 10% by mass, a reaction time of 45 minutes, a reaction temperature of 50° C., pH 6.0, and the amount of enzyme added to pulp that is 50 units/g, xylooligosaccharide having a polymerization degree of 1 or more and 15 or less and an average polymerization degree of approximately 5, and acidic xylooligosaccharide having a polymerization degree of 1 or more and 20-mer or less and an average polymerization degree of approximately 10 are eluted in molasses.

With regard to the reverse osmosis membrane treatment step, a sugar solution contained in the filtrate obtained after the reaction of pulp with hemicellulase is concentrated. In a method using a reverse osmosis membrane, low molecules such as xylose or xylobiose (sugar having a small polymerization degree) or low-molecular-weight substances contained in the molasses obtained after completion of the reaction (e.g., inorganic matters such as sodium carbonate or sodium thiosulfate, organic acids, etc.) are removed as permeates, and only high-molecular-weight substances (xylooligosaccharide having a high polymerization degree) are selectively concentrated.

An ultrafiltration membrane treatment is preferably performed on molasses that has been concentrated using a reverse osmosis membrane. In the treatment using an ultrafiltration membrane, high-molecular-weight impurities, such as raw material-derived lignin originally contained in the sugar concentrate or coloring substances, can be removed. The cutoff molecular weight of the ultrafiltration membrane is preferably 5000 or more and 30000 or less.

The molasses concentrated using a reverse osmosis membrane comprises xylooligosaccharide and acidic xylooligosaccharide. Some portions of the xylooligosaccharide and the acidic xylooligosaccharide bind to lignin and are present in the form of complexes (i.e., a lignin-xylooligosaccharide complex and a lignin-acidic xylooligosaccharide complex). Thus, an acid treatment is performed on the molasses that has been concentrated using a reverse osmosis membrane, so that xylooligosaccharide and acidic xylooligosaccharide can be released from the complexes. The acid treatment method is, for example, a method comprising adding acid to molasses to adjust pH to 5 or less, and then heating the molasses at a high temperature. The acid used in the adjustment of pH is not particularly limited, and examples of the acid include mineral acids such as sulfuric acid and hydrochloric acid, and organic acids such as oxalic acid and acetic acid. The pH applied during the acid treatment is preferably 2 or more and 5 or less. The temperature applied during the acid treatment is not particularly limited, and it is preferably 100° C. or higher and 200° C. or lower. In addition, the pressure applied during the acid treatment is preferably in the range of the atmospheric pressure or more and 5 kg/cm$^2$ or less.

In order to further reduce the content of impurities contained in the molasses after completion of the acid treatment, such as coloring substances, an activated carbon treatment is preferably carried out. The type of the activated carbon used is not particularly limited, as long as it has an ability to reduce the content of impurities contained in the molasses, such as coloring substances.

In the ion exchange treatment step, xylooligosaccharide and acidic xylooligosaccharide contained in molasses, from which impurities such as coloring substances have been reduced, are separated and/or purified using an ion exchange resin. The separation and/or purification method that can be applied herein is, for example, a method of passing a sugar concentrate containing oligosaccharide through (1) a strong cation resin, (2) a weak anion resin, (3) a strong cation resin, and (4) a weak anion resin in this order. Since acidic xylooligosaccharide is adsorbed on the anionic resin in this method, only xylooligosaccharide can be recovered as a filtrate. Subsequently, a salt solution such as sodium chloride is passed through the anion resin, so that acidic xylooligosaccharide can be eluted from the resin and can be recovered. The recovered solution containing xylooligosaccharide and acidic xylooligosaccharide can be concentrated, for example, using a concentration apparatus such as Evaporation. The solution containing oligosaccharide is dried by spray drying to obtain the powders of xylooligosaccharide and acidic xylooligosaccharide.

Xylan can be extracted by applying, for example, the method disclosed in JP-A-2012-180424.

Cellulose can be extracted by applying, for example, the method disclosed in JP-A-2014-148629.

<Formation of Derivative of Polymerization Unit (a)>

As a polymerization unit (a), the sugar moiety obtained by the above-described extraction method may be directly used, but the OH group of the sugar moiety may be modified by acetylation or halogenation and may be then used. For example, when an acetyl group is introduced into the sugar moiety, the sugar moiety is allowed to react with acetic anhydride, so that an acetylated sugar moiety can be obtained.

<Method of Synthesizing Polymerization Unit (b)>

The polymerization unit (b) may be formed by synthesis, or a commercially available product may be used as such a polymerization unit (b). In the case of polymerizing the polymerization unit (b), a known synthetic method can be adopted. On the other hand, in the case of using a commercially available product, Amino-terminated PS (Mw=12300 Da, Mw/Mn=1.02, manufactured by Polymer Source, Inc.), etc. can be used, for example.

<Coupling Reaction>

The block copolymer can be synthesized with reference to Macromolecules Vol. 36, No. 6, 2003. Specifically, a compound comprising the polymerization unit (a) and a compound comprising the polymerization unit (b) are added to a solvent such as DMF, water or acetonitrile, and a reducing agent is then added thereto. The reducing agent can be NaCNBH$_3$ or the like. Thereafter, the mixture is stirred at a temperature of 30° C. or higher and 100° C. or lower for 1 or more and 20 or less days, and a reducing agent is appropriately added to the reaction mixture, as necessary. Water is added to the reaction mixture to obtain a precipitate, and a solid content thereof is then vacuum-dried, so that a block copolymer can be obtained.

Examples of the method of synthesizing a block copolymer include synthetic methods using radical polymerization, RAFT polymerization, ATRP polymerization, click reaction, NMP polymerization, or living anion polymerization, as well as the above-described method.

The RAFT polymerization is a radical initiation polymerization reaction involving an exchange chain reaction of utilizing a thiocarbonylthio group. For example, there can be adopted a method comprising converting the OH group attached to position 1 at the terminus of xylooligosaccharide to a thiocarbonylthio group, and then allowing a styrene monomer to react with the resultant at a temperature of 30° C. or higher and 100° C. or lower to synthesize a block copolymer (Material Matters, Vol. 5, No. 1, *Saishin Kobunshi Gosei* (Latest Polymer Synthesis), Sigma-Aldrich Japan).

In the ATRP polymerization, the OH group at the terminus of sugar is halogenated, and thereafter, a metal complex [(CuCl, CuCl$_2$, CuBr, CuBr$_2$, CuI, etc.)+TPMA (tris(2-pyridylmethyl)amine)], MeTREN (tris[2-(dimethylamino)ethyl]amine), etc.), a monomer (e.g., a styrene monomer), and a polymerization initiator (2,2,5-trimethyl-3-(1-phenylethoxy)-4-phenyl-3-azahexane) are allowed to react with the sugar, so that a sugar block copolymer (e.g., a sugar-styrene block copolymer) can be synthesized.

The living anion polymerization is a method of carrying out a polymerization reaction by allowing a polymerization initiator such as n-BuLi to react with a monomer. For example, xylooligosaccharide, position β-1 at the terminus of which is halogenated, is allowed to react with a polymerization initiator, and thereafter, the resultant is then allowed to react with a styrene monomer, so that a xylooligosaccharide-styrene block copolymer can be synthesized.

The click reaction is a 1,3-dipolar azide/alkyne cycloaddition reaction of using sugar having a propargyl group and a Cu catalyst. The polymerization unit (a) and the polymerization unit (b) have a linking group comprising the following structure between them.

[Formula 20]

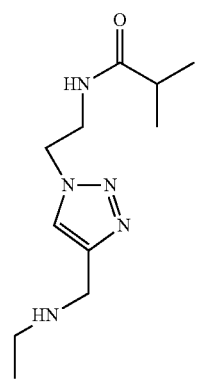

(Pattern Forming Method)

The present invention relates to a pattern forming method, comprising a step of applying the aforementioned self-assembly composition for pattern formation onto a substrate and forming a self-assembly film according to self-assembly phase separation, and an etching step. The step of forming a self-assembly film according to self-assembly phase separation is a step of forming a self-assembly film having a phase-separated structure, using a self-assembly composition for pattern formation (hereinafter also referred to as a "step (1)"). The etching step is a step of removing a partial phase of the self-assembly film (hereinafter also referred to as a "step (2)").

Besides, the step of forming a self-assembly film may further comprise a step of forming a guide pattern on the substrate, before the step of forming the self-assembly film. The step of forming a guide pattern may comprise a step of forming a under layer and a step of forming a guide pattern on the under layer. Moreover, the step of forming a guide pattern may also comprise a step of forming a under layer on the guide pattern.

FIG. 1 to FIG. 4 are schematic views showing the pattern-forming step. FIG. 1 shows a pattern forming method in a case where a guide hole 50 is formed as a guide pattern on a substrate 70. When the pattern-forming step includes a step of forming a guide pattern, as shown in FIG. 1(a), the guide hole 50 having a hole part 55 is formed as a guide pattern on the substrate 70. The hole part 55 in the guide hole 50 is filled with a self-assembly composition for pattern formation 1 comprising a block copolymer 10.

FIG. 2 shows a pattern forming method in a case where linear, uneven shaped guide patterns 60 are formed on a substrate 70. In FIG. 2(a), a space (groove) between the guide patterns 60 is filled with a self-assembly composition for pattern formation 1 comprising a block copolymer 10.

FIG. 3 shows a pattern forming method in a case where post guides 62 are formed as guide patterns on a substrate 70 having a under layer 80. In FIG. 3(a), a self-assembly composition for pattern formation 1 comprising a block copolymer 10 is filled into a substrate 70, such that the post guides 62 are embedded into the self-assembly composition.

FIG. 4 shows a pattern forming method in a case where a guide hole 50 is formed as a guide pattern on a substrate 70 having a under layer 80. In FIG. 4, a hole part 55 in a guide hole 50 is filled with a self-assembly composition for pattern formation 1 comprising a block copolymer 10. Besides, a difference between FIG. 1 and FIG. 4 is that one phase P and one phase Q are formed in the hole part 55 in FIG. 1, whereas a plurality of phases Q are formed in FIG. 4. FIG. 4 shows a pattern forming method in a case where the diameter of the guide hole 50 is longer than the molecular length of the block copolymer 10. In FIG. 4, the number of phases Q formed in the hole part 55 is preferably 2 or more and 500 or less, more preferably 2 or more and 50 or less, and further preferably 1 or more and 7 or less. By setting the number of phases Q formed in the hole part 55 within the above-described range, a pattern is easily formed to have a desired shape.

The guide pattern may have a hole shape as shown in FIG. 1, or may also have a linear, uneven shape as shown in FIG. 2. When the guide pattern has a hole shape, the preferred internal diameter is, for example, preferably 5 nm or more and 300 nm or less, and more preferably 6 nm or more and 200 nm or less. When the guide pattern has a linear, uneven shape, the width of a concave portion is preferably 5 nm or more and 300 nm or less, and more preferably 6 nm or more and 200 nm or less. The guide pattern needs to have a pattern shape that is greater than a pattern to be formed.

The hole shape of the guide hole may be a perfect circle or an ellipse. Otherwise, the hole shape may also be a plurality of perfect circles that are connected with one another. Based on the relationship between the molecular length (L0) of the block copolymer and the size (diameter) of the guide hole, a phase-separated shape varies in the guide hole. In the case of the hole shape as shown in FIG. 1, the diameter of the hole is preferably 1.5 to 2.5 times larger than the molecular length L0 of the block copolymer. Herein, the molecular length L0 of the block copolymer can be measured using a small-angle X-ray scattering method (SAXS). Moreover, in the case of the hole shape as shown in FIG. 4, the length of the major axis of the ellipse of the guide hole is preferably 3 to 5 times longer than the molecular length L0 of the block copolymer, and the length of the minor axis of the ellipse of the guide hole is preferably 1.5 to 2.5 times longer than the molecular length L0 of the block copolymer.

The diameter of the post guide 62 as shown in FIG. 3 is preferably 5 nm or more and 300 nm or less, and more preferably 6 nm or more and 200 nm or less. Moreover, the height of the post guide 62 is preferably 5 nm or more and 300 nm or less, and more preferably 6 nm or more and 200 nm or less.

The post guide 62 can be appropriately arranged, such that a desired phase-separated pattern structure can be obtained. The post guide 62 may be arranged, such that the arrangement pattern can be a hexagonal lattice arrangement. In the case of such a hexagonal lattice arrangement, the preferred interval between the post guides 62 is preferably 1.5 to 20 times, more preferably 1.5 to 10 times, and further preferably 1.5 to 7 times larger than the molecular length L0 of the block copolymer. As the interval between the post guides 62 decreases, a phase-separated pattern having higher positional accuracy can be obtained.

Besides, as a guide pattern forming method, a physical guide (graphoepitaxy) as described in FIGS. 1 to 4 may be used, or a chemical guide (chemical epitaxy) may also be used. As a method of forming a chemical guide, the method described in Japanese Patent No. 5729537 can be applied, for example.

The material of the guide pattern is not particularly limited. For example, inorganic materials such as Si, $SiO_2$, $Al_2O_3$, AlN, GaN or glass may be used, or commercially available resist materials may also be used.

Examples of the substrate used in the pattern forming method of the present invention include substrates such as glass, silicone, SiN, GaN or AlN. Otherwise, substrates consisting of organic materials such as PET, PE, PEO, PS, a cycloolefin polymer, polylactic acid or a cellulose nanofiber may also be used. Moreover, a plurality of layers consisting of different materials may be sandwiched between the substrate and the guide pattern-forming layer. Such materials are not particularly limited, and examples of the materials include inorganic materials such as $SiO_2$, SiN, $Al_2O_3$, AlN, GaN, GaAs, W, SOC or SOG, and organic materials such as commercially available adhesives.

When the step of forming a guide pattern includes a step of forming a under layer, as a composition for forming a under layer, a commercially available composition for forming a under layer can be used.

The method of forming a under layer is not particularly limited. The method of forming a under layer is, for example, a method comprising applying a composition for forming a under layer onto a substrate according to a known method such as spin-coating to form a coated film, and then hardening the coated film by light exposure and/or heating, so as to form a under layer. Examples of the radiation used in the light exposure include visible light, ultraviolet light, far-ultraviolet light, X-ray, electron beam, γ-ray, molecular beam, and ion beam. In addition, the temperature applied upon heating the coated film is not particularly limited, and it is preferably 90° C. or higher and 550° C. or lower. Besides, the film thickness of the under layer is not particularly limited, and it is preferably 10 nm or more and 20000 nm or less. Further, the above-described under layer may comprise a SOC (Spin on carbon) film.

When the step of forming a guide pattern includes a step of forming a under layer and a step of forming a guide pattern on the under layer, a method similar to a known resist pattern forming method can be applied. As a composition for forming a guide pattern, a conventional composition for forming a resist film can be used. As a specific method of forming a guide pattern, for example, a commercially available chemically amplified resist composition is applied onto the above-described under layer to form a resist film. Subsequently, radiation is applied to a desired region of the resist film via a mask with a specific pattern, and immersion exposure, etc. is then carried out. Examples of the above-described radiation include ultraviolet light, far-ultraviolet light, X-ray, and charged particle beam. Among these, far-ultraviolet light is preferable, ArF excimer laser light and KrF excimer laser light are more preferable, and ArF excimer laser light is further preferable. Subsequently, post-exposure baking (PEB) is carried out, and development is then carried out using a developing solution such as an alkaline developing solution, so as to form a desired guide pattern. Moreover, the guide pattern can also be formed by applying a nanoimprint technique.

Besides, a hydrophobic treatment or a hydrophilic treatment may be performed on the surface of the above-described guide pattern. The specific treatment method is, for example, a hydrogenation treatment, in which the surface of the guide pattern is exposed to hydrogen plasma for a predetermined period of time. By enhancing the hydrophobicity or hydrophilicity of the surface of the guide pattern, the self-assembling of the self-assembly composition for pattern formation can be promoted.

By allowing the pattern forming method to comprise a step of forming a under layer and a step of forming a guide pattern on the under layer, the phase separation of a self-assembly composition for pattern formation is precisely controlled, and the obtained pattern can be further fibrillated. In the case of using the self-assembly composition for pattern formation of the present invention, a fine pattern, in which phase separation is precisely controlled, can be formed without forming a under layer. Furthermore, even if a guide pattern is not formed, a phase-separated structure can be formed.

<Step (1)>

The step of forming a self-assembly film according to self-assembly phase separation (step (1)) is a step of forming a self-assembly film having a phase-separated structure, using a self-assembly composition for pattern formation. In a case where the aforementioned under layer and guide pattern are not used, the self-assembly composition for pattern formation is directly applied onto a substrate to form a coated film, so as to form a self-assembly film having a phase-separated structure. On the other hand, in a case where the aforementioned under layer and guide pattern are used, a self-assembly composition for pattern formation is used to form a coated film in a region on the under layer sandwiched between the guide patterns, and a self-assembly film with a phase-separated structure, which has an interface roughly vertical to the substrate, is formed on an under-layer film formed on the substrate. The present invention may relate to such a self-assembly film.

In the step (1), annealing or the like is carried out on the self-assembly composition for pattern formation that has been applied onto the substrate, so that polymers having the same properties are accumulated with one another to spontaneously form an order pattern, thereby forming a self-assembly film having a phase-separated structure such as a sea-island structure, a cylinder structure, a co-continuous structure or a lamellar structure. Since the self-assembly composition for pattern formation of the present invention has high cohesive power and can form a favorable phase-separated structure, it becomes possible to achieve sufficient phase separation in a shorter annealing time.

The annealing method is, for example, a method of heating the self-assembly composition for pattern formation at a temperature of 80° C. or higher and 400° C. or lower, using an oven, a hot plate, a microwave, etc. The annealing time is generally 10 seconds or longer and 30 minutes or shorter. With regard to annealing conditions, as the content of the sugar moiety increases, it becomes possible to shorten the annealing time or to decrease the annealing temperature. For example, when the self-assembly composition for pattern formation is heated with a hot plate, it is preferable to carry out the annealing treatment at a temperature of 100° C. or higher and 300° C. or lower, for 10 seconds or more and 20 minutes or less. Moreover, the film thickness of the self-assembly film obtained by the step (1) is preferably 0.1 nm or more and 1000 nm or less, and more preferably 0.1 nm or more and 500 nm or less.

The annealing step is preferably established, in FIG. 1, when the condition shown in FIG. 1(*a*) is converted to the condition shown in FIG. 1(*b*), or in FIG. 2, when the condition shown in FIG. 2(*a*) is converted to the condition shown in FIG. 2(*b*), or in FIG. 3, when the condition shown in FIG. 3(*b*) is converted to the condition shown in FIG. 3(*c*), or in FIG. 4, when the condition shown in FIG. 4(*b*) is converted to the condition shown in FIG. 4(*c*). By phase separation of the block copolymer in the annealing step, a phase-separated structure is formed. When the pattern-forming step includes a step of forming a guide pattern, as shown in FIG. 1(*b*) for example, the phase is separated into the phase P on the outer peripheral side and the phase Q on the inner peripheral side. At this time, phase separation is preferably carried out, so that the block copolymer becomes a cylindrical shape. When the guide pattern has a linear, uneven shape, the separated phase P and the separated phase Q are separated from each other in layers, as shown in FIG. 2(*b*). At this time, phase separation is preferably carried out, so that the block copolymer becomes a lamellar shape. In FIG. 3(*c*), the phase is separated into the phase P on the outer peripheral side and the phase Q on the inner peripheral side, so that a hexagonal close-packed structure can be formed having the post guide 62 as a center. On the other hand, in FIG. 4(*c*), the phase P is separated from the phase Q, so that a plurality of the phases Q can be formed in the guide hole 50. In the present invention, the phase P is preferably composed of a polymerization unit (b) comprising at least two or more aromatic ring-containing units, and the phase Q is preferably composed of a polymerization unit (a) comprising two or more units of at least one type selected from a glucose unit and a xylose unit. Besides, when not a hole pattern, but a pillar pattern is to be formed in FIG. 1, FIG. 3, and FIG. 4, the phase P is preferably composed of a polymerization unit (a) comprising two or more units of at least one type selected from a glucose unit and a xylose unit, and the phase Q is preferably composed of a polymerization unit (b) comprising at least two or more aromatic ring-containing units.

The method of applying the self-assembly composition for pattern formation onto a substrate to form a coated film is not particularly limited. An example of the method of forming such a coated film is a method of applying the used self-assembly composition for pattern formation onto a substrate according to a spin-coating method. According to this method, the self-assembly composition for pattern formation is applied onto the above-described substrate, or between guide patterns on the above-described under layer, thereby forming a coated film.

<Step (2)>

The etching step (step (2)) is a step of removing a partial phase from the self-assembly film. This removal is carried out by an etching treatment of utilizing a difference in the etching rates of individual phases that have been separated by self-assembling (P and Q in FIGS. 1 and 2). FIG. 1(c) and FIG. 2(c) show the state of a phase-separated structure, from which the phase Q has been removed.

Examples of the method of removing a partial phase from the self-assembly film by the etching step include known etching methods including: reactive ion etching (RIE) such as chemical dry etching or chemical wet etching (wet development); and physical etching such as sputter etching or ion beam etching. Among these etching methods, for example, a dry etching step using $O_2$ gas or the like is preferably adopted as a method of removing a phase consisting of a polymerization unit comprising two or more units of at least one type selected from a glucose unit and a xylose unit. A chemical wet etching step is also preferably adopted.

The etching step may comprise a step of removing a guide pattern. The method of removing a guide pattern is not particularly limited. For example, a method of removing a guide pattern by an etching treatment of utilizing a difference in the etching rates between the guide pattern and the formed self-assembly film can be applied.

Before the etching step, a process of introducing a metal into a hydrophilic portion (sugar moiety), such as an SIS process (Sequential Infiltration Synthesis), may be established. Examples of the metal to be introduced include Li, Be, Na, Mg, Al, Si, K, Ca, Sc, Ti, V, Cr, Mn, Fe, Co, Ni, Cu, Zn, Ga, Ge, As, Rb, Sr, Y, Zr, Nb, Mo, Ru, Pd, Ag, Cd, In, Sn, Sb, Te, Cs, Ba, La, Hf, Ta, W, Re, Os, Ir, Pt, Au, Hg, Tl, Pb, Bi, Po, Ce, Pr, Nd, Pm, Sm, Eu, Gd, Tb, Dy, Ho, Er, Tm, Yb, and Lu. Such a process can be carried out according to the method described, for example, in Journal of Photopolymer Science and Technology Volume 29, Number 5 (2016) 653-657. In such a case, not a hydrophilic portion but a hydrophobic portion is removed by the etching step.

The pattern can be formed as described above. The formed pattern is preferably a line-and-space pattern, a hole pattern, or a pillar pattern. According to the pattern forming method of the present invention, since the aforementioned self-assembly composition for pattern formation is used, a favorable phase-separated structure can be formed even in the case of forming a large size pattern. In addition, upon the formation of a fine pattern structure, a under layer and the like are not necessary, and a pattern can be formed in a simple process. Moreover, according to the improvement of phase separation performance, it becomes possible to reduce roughness (unevenness) at the edge after the formation of a pattern.

EXAMPLES

The characteristics of the present invention will be more specifically described in the following examples and comparative examples. The materials, used amounts, ratios, treatment contents, treatment procedures, etc. can be appropriately modified, unless they are deviated from the gist of the present invention. Accordingly, the scope of the present invention should not be restrictively interpreted by the following specific examples.

Example 1

<Synthesis of sugar methacrylate>33 g of Xylooligosaccharide (average polymerization degree: 10) was dissolved in 150 mL of water, and 28.5 g each of ammonium hydrogen carbonate was added to the solution every 24 hours, four times. The obtained mixture was stirred at 37° C. for 96 hours. Thereafter, 200 mL of distilled water was added to the reaction mixture, and water was distilled away to result in a volume of 20 mL. After that, 150 mL of water was added to the reaction mixture, and the obtained mixture was then concentrated to a volume of 10 mL. These operations were carried out repeatedly, until ammonia odor disappeared. The resultant was freeze-dried to obtain a white solid. This substance was examined by FT-IR, and as a result, an NH-derived peak was observed around 1500 $cm^{-1}$. Thus, it was confirmed that the substance could be aminated.

This substance was dissolved in 50 mL of a $1\times10^{-3}$M KOH aqueous solution, and 10.4 g of 2-isocyanate ethyl methacrylate was then added to the solution. The obtained solution was intensively stirred for 12 hours, while the temperature was kept at 3° C. The precipitated white solid was removed, and the filtrate was then washed using 50 mL of diethyl ether four times, followed by performing freeze-drying. Thereafter, the obtained white solid was dissolved in a mixed solution consisting of 2 mL of water and 10 mL of methanol, and the thus obtained solution was then added dropwise to a mixed solution of 200 mL of acetone, followed by cooling. Thereafter, the reaction solution was filtrated through a filter, and was then dried under reduced pressure, to obtain 2-(methacryloyloxy)ethyl ureide xylooligosaccharide.

[Formula 21]

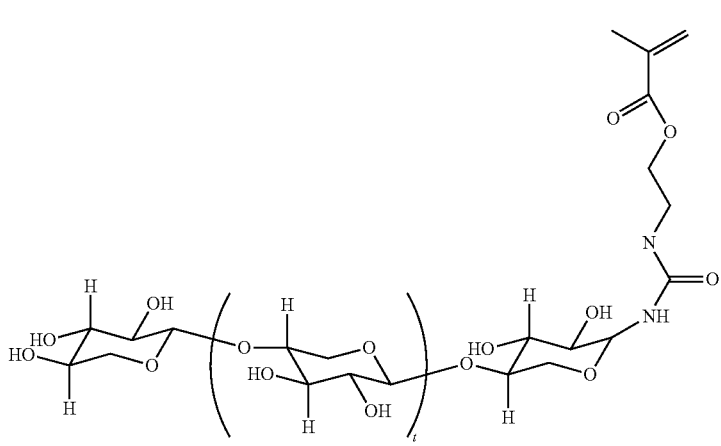

From the FT-IR spectrum, a peak derived from NH—CO—NH mutual stretching was found at 1570 cm$^{-1}$, a peak derived from C=O (urea) stretching vibration was found at 1650 cm$^{-1}$, and a peak derived from C=O (ester) stretching vibration was found at 1705 cm$^{-1}$. Thus, it was confirmed that sugar methacrylate could be synthesized.

<Polystyrene>

The inside of a reactor A was evacuated, and thereafter, a styrene solution (2 g, 19.2 mmol) comprising purified copper(I) bromide (28 mg, 0.192 mmol), 4,4'-di-n-heptyl-2,2'-bipyridine (dIIbipyy) (0.135 g, 0.384 mmol) and 1-phenylethyl bromide (36 mg, 0.192 mmol) was added to the reactor. The mixed solution was deaerated under freeze-drying conditions. Thereafter, while deaerating, the temperature of the reaction system was increased to 110° C., to obtain a polystyrene solution having the following structure. After completion of the polystyrene reaction, the reaction system was cooled to room temperature.

[Formula 22]

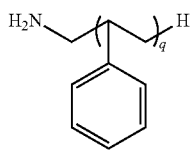

<Synthesis of PS-Sugar Methacrylate Block Copolymer>

Sugar methacrylate and polystyrene having the unit ratio shown in Table 1 were prepared, and thereafter, a block copolymer having the molecular weight shown in Table 1 was synthesized according to ATRP polymerization. Polymerization was carried out using an H-type vessel, in which a reactor A was connected with a reactor B via a glass tube.

Purified copper(I) bromide (21.4 g, 0.096 mmol), dHbipyy (68 mg, 0.192 mmol), a sugar methacrylate compound (19.2 g, 19.2 mmol) and 1,2-dimethoxybenzene (6.3 g) were added to the reactor B, followed by deaeration. The solution contained in the reactor B was added to the polystyrene solution contained in the reactor A through the glass tube. While deaerating and stirring, the reaction was carried out at 80° C. for 24 hours, and the reaction mixture was then recrystallized from chloroform and methanol to obtain a PS-sugar methacrylate block copolymer.

[Formula 23]

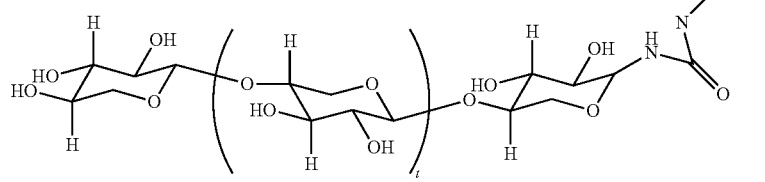

wherein p=11, q=29, and t=8.

Examples 2 and 3

In Example 2, sugar methacrylate was synthesized by using xylotetraose, instead of xylooligosaccharide. In addition, in Example 3, sugar methacrylate was synthesized by using xylotriose, instead of xylooligosaccharide. Polystyrene was polymerized, so that the unit ratio shown in Table 1 could be obtained. The polymerization degree of polystyrene was adjusted depending on the reaction time, and whether or not desired polystyrene could be polymerized was confirmed using a GPC column. Except for these conditions, a PS-sugar methacrylate block copolymer was obtained in the same manner as that of Example 1.

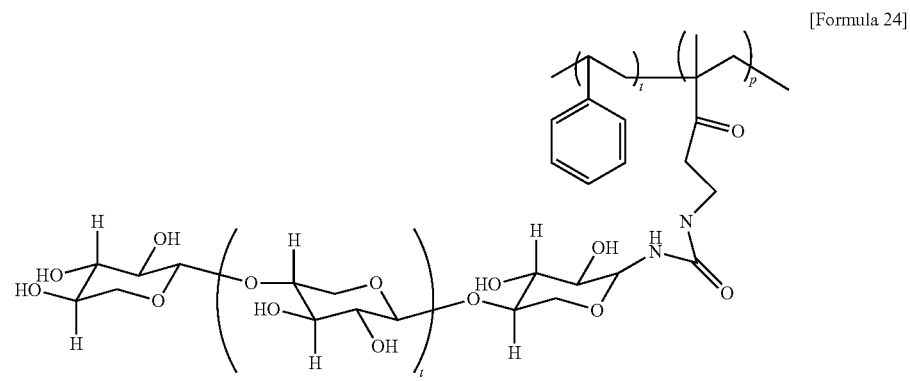

[Formula 24]

wherein p=21, q=49, and t=2 (Example 2), or p=27, q=41, and t=1 (Example 3).

Example 4

<Synthesis of Acetyl Sugar Methacrylate>

The sugar methacrylate (10 g) synthesized in the same manner as that of Example 1 was allowed to react with 120 g of acetic anhydride for 2 hours. Thereafter, the reaction was terminated by addition of a 33% magnesium acetate solution, and pure water was then added to the reaction mixture to precipitate acetyl sugar methacrylate.

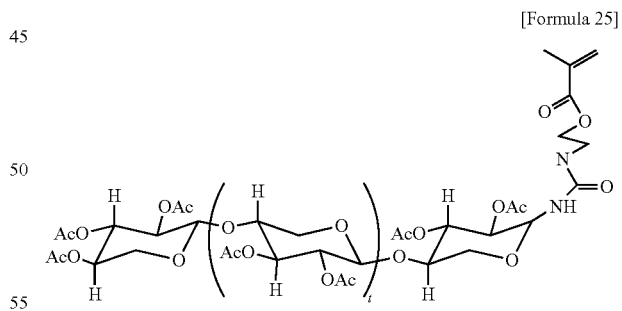

[Formula 25]

<Synthesis of PS-Acetyl Sugar Methacrylate Block Copolymer>

Polystyrene was polymerized in the same manner as that of Example 1, with the exception that the additive amount of styrene and the polymerization time were adjusted so that the unit ratio and molecular weight shown in Table 1 could be obtained. Thereafter, a PS-acetyl sugar methacrylate block copolymer was synthesized according to ATRP polymerization.

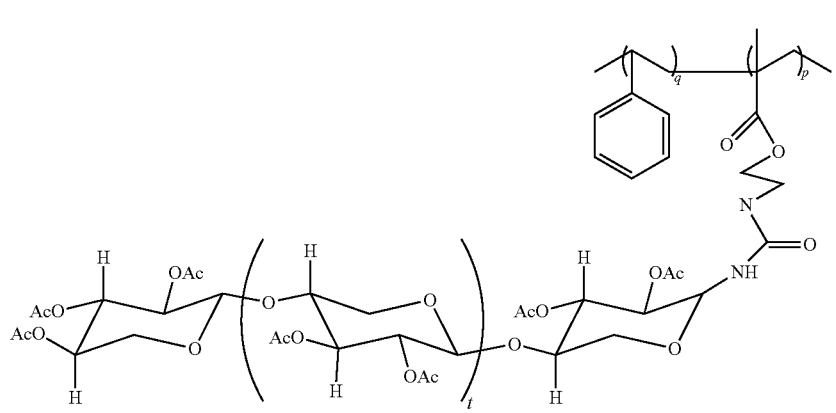

wherein p=7, q=29, and t=8.

Example 5

A PS-acetyl sugar methacrylate block copolymer was synthesized in the same manner as that of Example 4, with the exception that the polymerization time of polystyrene and the like were adjusted so that the unit ratio shown in Table 1 could be obtained.

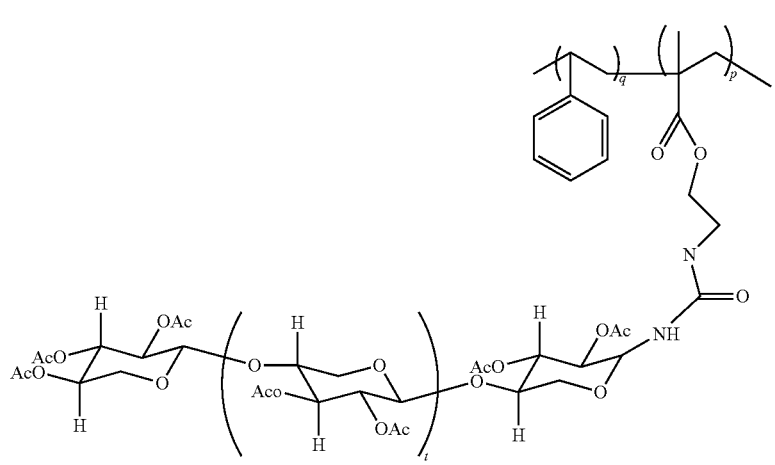

wherein p=35, q=160, and t=8.

Example 6

<Synthesis of Poly(4-Trimethylsilylstyrene (PTMSS))>

Poly(4-trimethylsilylstyrene (PTMSS)) was synthesized in accordance with Journal of polymer science part B Polymer Physics 43, 1214-1219. For polymerization, the ATRP polymerization method was applied. Trimethylsilylstyrene (10 g), 520 mg of 2-(bromomethyl)-2-methylbutanoic acid, 5 mg of copper bromide, 52 mg of Me6TREN, and 20 mL of toluene were added into a round-bottom flask. The solution was deaerated with argon for 10 minutes, and thereafter, 50 mg of tin(II) ethylhexanoate was added thereto. The obtained solution was heated to 90° C., and polymerization was carried out for 4 hours. The polymer was precipitated in methanol, and was then dried in vacuum to obtain 5.2 g of poly(trimethylsilyl)styrene.

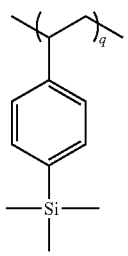

<Synthesis of PTMSS-Acetyl Sugar Methacrylate Block Copolymer>

Acetyl sugar methacrylate (average polymerization degree of sugar: 4) and PTMSS having the unit ratio shown in Table 1 were prepared, and thereafter, a PTMSS-acetyl sugar methacrylate block copolymer having the molecular weight shown in Table 1 was synthesized according to ATRP polymerization.

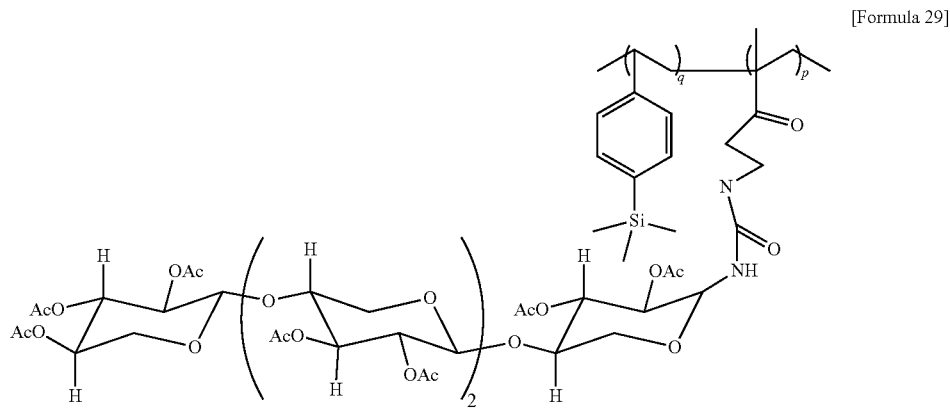

[Formula 29]

wherein p=56 and q=224.

Example 7

<Synthesis of Acetyl Sugar Styrene>

Acetyl sugar was synthesized in the same manner as the synthesis of acetyl sugar methacrylate in Example 4, with the exception that xylooligosaccharide having an average polymerization degree of 4 was used instead of sugar methacrylate. Subsequently, 10.8 g (90 mmol) of 4-vinylphenol, 32.2 g (32 mmol) of acetyl sugar, and 0.5 g of zinc chloride were heated in a hot water bath at 160° C. for 30 minutes, while fully stirring. The molten mixture was cooled to approximately 60° C., and was then dissolved in 200 mL of benzene. The obtained solution was washed with water twice, and was then washed with 1 M sodium hydroxide, until the water phase became almost colorless, and was further washed with water twice. The resultant was dried, and was then concentrated under reduced pressure to obtain 26.5 g of acetyl sugar styrene having

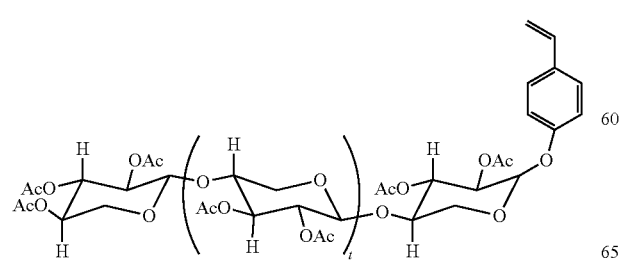

[Formula 30]

<Synthesis of PTMSS-Acetyl Sugar Styrene Block Copolymer>

Acetyl sugar styrene and PTMSS having the unit ratio shown in Table 1 were prepared, and thereafter, a PTMSS-acetyl sugar styrene block copolymer having the molecular weight shown in Table 1 was synthesized according to ATRP polymerization.

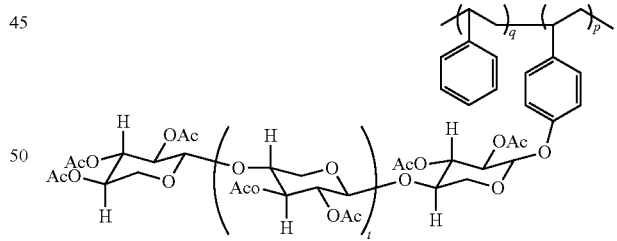

[Formula 31]

wherein p=58, q=231, and t=2.

Example 8

A PTMSS-(acetyl sugar styrene-ran-hydroxystyrene) block copolymer was synthesized in the same manner as that of Example 7, with the exceptions that a mixture of hydroxystyrene and acetyl sugar styrene (mixing ratio of 2:1) was used instead of acetyl sugar styrene, and that the molecular weight was adjusted as shown in Table 1.

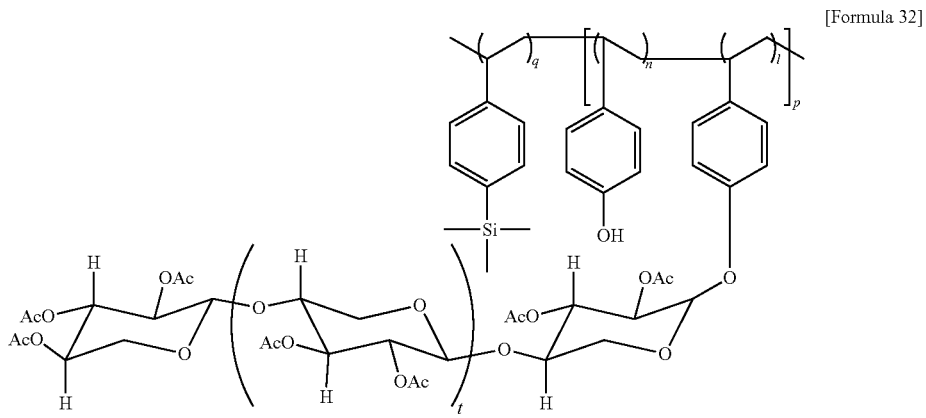

[Formula 32]

wherein p=1, q=385, n=64, l=32, and t=2.

Example 9

A PS-sugar methacrylate block copolymer was synthesized in the same manner as that of Example 1, with the exception that the additive amounts of sugar methacrylate with xylose and polystyrene were changed to have the unit ratio shown in Table 1.

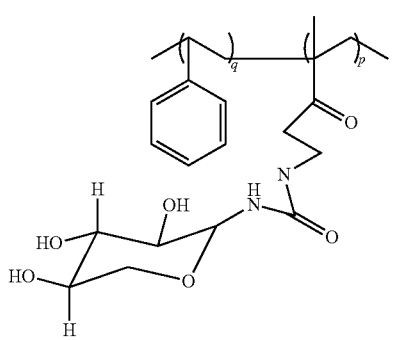

[Formula 33]

wherein p=49 and q=49.

Example 10

A PTMSS-acetyl sugar styrene block copolymer was synthesized in the same manner as that of Example 7, with the exceptions that the additive amounts of acetyl sugar styrene (average polymerization degree of sugar: 3) and PTMSS were changed to have the unit ratio shown in Table 1, and that the polymerization time was changed to have the molecular weight shown in Table 1.

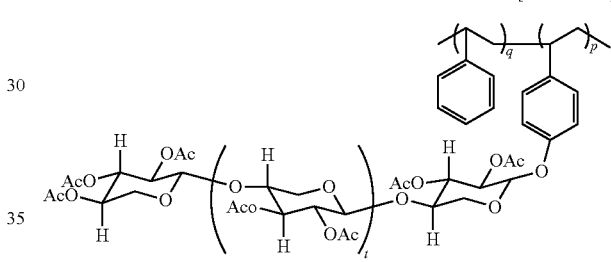

[Formula 34]

wherein p=13, q=13, and t=1.

Example 11

To a flask, 500 mL of tetrahydrofuran and 92 g of a THF solution (manufactured by Tokyo Chemical Industry Co., Ltd.) containing 2.6% by mass of lithium chloride were added, and the obtained mixture was then cooled to −78° C. in an argon atmosphere. Thereafter, 13 g of a hexane solution (manufactured by Tokyo Chemical Industry Co., Ltd.) containing 15.4% by mass of n-butyllithium was added to the reaction mixture, and the obtained mixture was then stirred for 5 minutes, followed by performing a dehydration/deaeration treatment. Subsequently, 18.8 g of styrene (manufactured by Wako Pure Chemical Industries, Ltd.) was added to the reaction mixture, and the thus obtained mixture was then stirred for 30 minutes. Thereafter, 1 g of diphenylethylene (manufactured by Wako Pure Chemical Industries, Ltd.) was further added to the reaction mixture, followed by stirring for 5 minutes. Thereafter, 438 g of acetyl sugar methacrylate having an average polymerization degree of sugar that was 3 was added to the reaction mixture, and the thus obtained mixture was further stirred for 90 minutes. After that, 7 g of methanol was added to the reaction mixture to terminate the reaction. The obtained block copolymer was washed, filtrated, and concentrated. The structure of the PS-acetyl sugar methacrylate block copolymer is as follows.

[Formula 35]

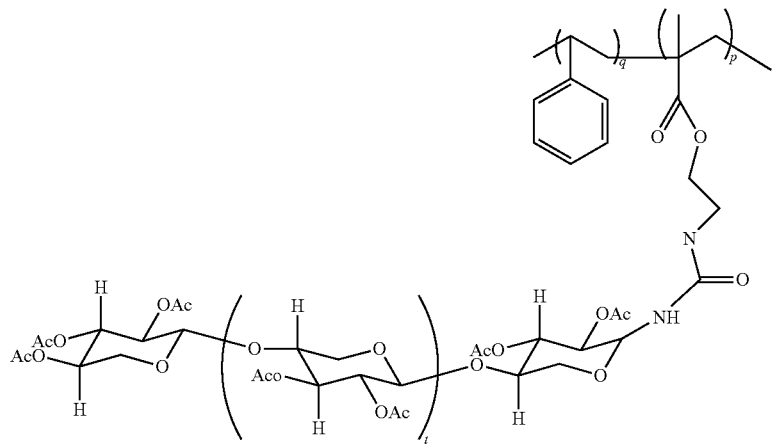

wherein q=94, p=220, and t=1.

Example 12

PS-acetyl sugar methacrylate was synthesized in the same manner as that of Example 11, with the exceptions that acetyl sugar methacrylate comprising xylose was used, instead of acetyl sugar methacrylate having an average polymerization degree of sugar of 3, and that the reaction time was adjusted to have the molecular weight shown in Table 1.

[Formula 36]

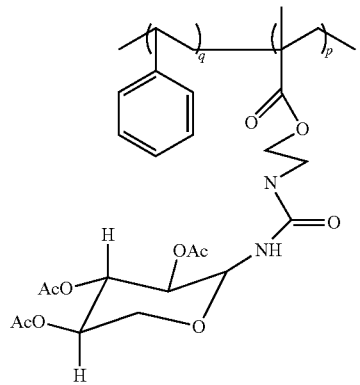

wherein p=42 and q=18.

Example 13

<Synthesis of Acetyl Sugar Methacrylate 2>

10 g of Xylooligosaccharide (average polymerization degree: 2) was added to a mixed solution of 120 g of acetic anhydride and 160 g of acetic acid, and the obtained solution was then stirred at 30° C. for 2 hours. Approximately five times amount of cold water was slowly added to the reaction solution, while stirring, and the obtained mixture was then stirred for 2 hours. Thereafter, the reaction mixture was left at rest overnight. The precipitated crystal (10 g) was added to a solution prepared by adding 0.6 g of ethylenediamine and 0.7 g of acetic acid to 200 mL of THF in a flask and setting the temperature at 0° C., and the obtained mixture was then stirred for 4 hours. This reaction mixture was poured into 500 mL of cold water, and was then extracted with dichloromethane twice. The obtained extract (10 g), 150 mL of dichloromethane and 2.4 g of triethylamine were added into a flask, and were then cooled to −30° C. Thereafter, 1.4 g of methacryloyl chloride was added to the reaction mixture, and the thus obtained mixture was then stirred for 2 hours. The obtained reaction mixture was poured into 150 mL of cold water, and was the extracted with dichloromethane twice, and the solvent was then concentrated to obtain 8.1 g of acetyl sugar methacrylate 2.

[Formula 37]

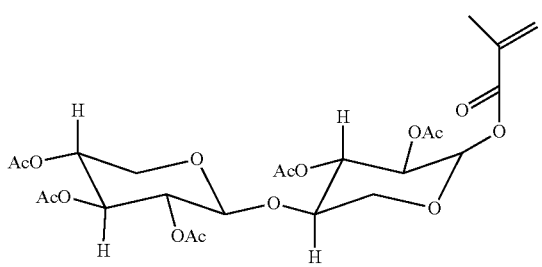

<Synthesis of PS-Acetyl Sugar Methacrylate 2 Block Copolymer>

500 mL of Tetrahydrofuran and 92 g of a THF solution (manufactured by Tokyo Chemical Industry Co., Ltd.) containing 2.6% by mass of lithium chloride were added into a flask, and the obtained mixture was then cooled to −78° C. in an argon atmosphere. Thereafter, 13 g of a hexane solution (manufactured by Tokyo Chemical Industry Co., Ltd.) containing 15.4% by mass of n-butyllithium was added to the reaction mixture, and the obtained mixture was then stirred for 5 minutes, followed by performing a dehydration/deaeration treatment. Subsequently, 18.8 g of styrene (manufactured by Wako Pure Chemical Industries, Ltd.) was added to the reaction mixture, and the thus obtained mixture was stirred for 15 minutes. Thereafter, 1 g of diphenylethylene (manufactured by Wako Pure Chemical Industries, Ltd.) was further added to the reaction mixture, followed by stirring for 5 minutes. Thereafter, 188 g of acetyl sugar methacrylate 2 was added to the reaction mixture, and the thus obtained mixture was further stirred for 15 minutes. After that, 7 g of methanol was added to the reaction mixture to terminate the reaction. The obtained block copolymer was washed, filtrated, and concentrated. The structure of the PS-acetyl sugar methacrylate 2 block copolymer is as follows.

to the reaction mixture, and the obtained mixture was then stirred for 5 minutes, followed by performing a dehydration/deaeration treatment. Subsequently, 48 g of styrene (manufactured by Wako Pure Chemical Industries, Ltd.) was added to the reaction mixture, and the thus obtained mixture was stirred for 1 hour. Thereafter, 1 g of diphenylethylene was further added to the reaction mixture, followed by stirring for 5 minutes. Thereafter, a mixture consisting of 35 g of acetyl sugar methacrylate 2 having an average polymerization degree of sugar that was 3 and 20 g of methyl methacrylate (manufactured by Wako Pure Chemical Industries, Ltd.) was added to the reaction mixture, and the thus obtained mixture was further stirred for 30 minutes. After that, 14 g of methanol was added to the reaction mixture to terminate the reaction. The obtained block copolymer was washed, filtrated, and concentrated. The structure of the PS-(acetyl sugar methacrylate 2-ran-methyl methacrylate) block copolymer is as follows.

[Formula 39]

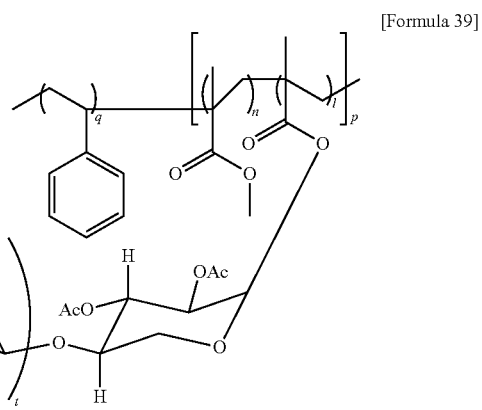

wherein q=1105, p=1, n=374, l=100, and t=1.

[Formula 38]

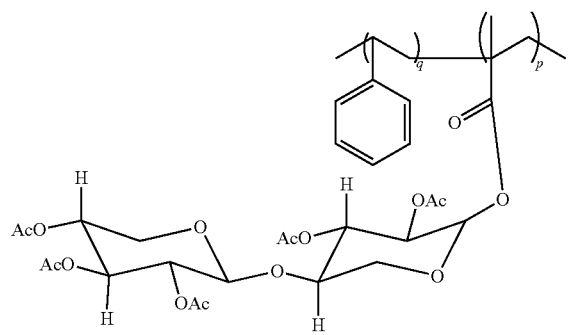

wherein q=30 and p=30.

Example 14

<Synthesis of PS-(Acetyl Sugar Methacrylate 2-Ran-Methyl Methacrylate) Block Copolymer>

To a flask, 1000 mL of tetrahydrofuran and 92 g of a THF solution (manufactured by Tokyo Chemical Industry Co., Ltd.) containing 2.6% by mass of lithium chloride were added, and the obtained mixture was then cooled to −78° C. in an argon atmosphere. Thereafter, 13 g of a hexane solution (manufactured by Tokyo Chemical Industry Co., Ltd.) containing 15.4% by mass of n-butyllithium was added Example 15

PS-(sugar methacrylate-ran-methyl methacrylate) was synthesized in the same manner as that of Example 2, with the exception that sugar methacrylate with xylose and methyl methacrylate were mixed at a ratio of 1:10, instead of the sugar methacrylate of Example 2, and were then adjusted so that the molecular weight and the ratio of polymerization units shown in Table 1 could be obtained.

[Formula 40]

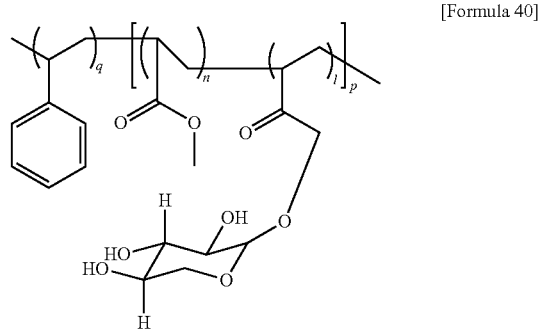

wherein p=1, q=129, n=50, and l=5.

Comparative Example 1

PS-PMMA was synthesized, so that it could have a molecular weight of 19500 and the ratio of polymerization units that was 7:3.

Comparative Example 2

PS-(sugar methacrylate-ran-methyl methacrylate) was synthesized in the same manner as that of Example 15, with the exception that sugar methacrylate and methyl methacrylate were mixed at a ratio of 1:18, so that it could have a molecular weight of 20000 and the ratio of polymerization units that was 7:3.

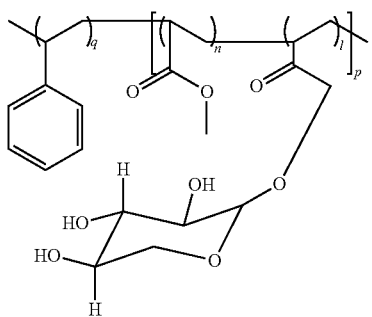

[Formula 41]

wherein p=1, q=132, n=54, and 1=3.

Comparative Example 3

PS-sugar methacrylate was synthesized, so that it could have a molecular weight of 21000 and the ratio of polymerization units that was 1:1.

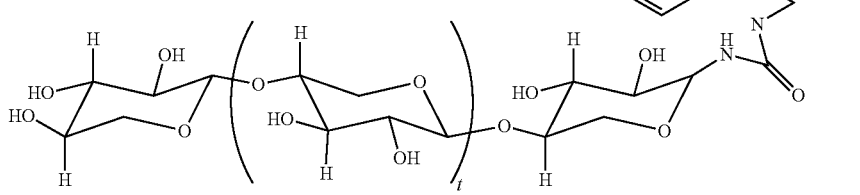

[Formula 42]

wherein p=12, q=12, and t=9.

(Evaluation and Analysis)

<Molecular Weight>

The weight average molecular weight of a block copolymer was measured by a gel permeation chromatography (GPC) method.
GPC column: Shodex K-806M/K-802 coupled column (manufactured by SHOWA DENKO K. K)
Column temperature: 40° C.
Mobile phase: chloroform
Detector: RI When a block copolymer was synthesized, a first block (polymerization unit (a)) was first polymerized. Thereafter, a portion was removed from the first block, and the polymerization degree thereof was then confirmed by the GPC method. Thereafter, a second block (polymerization unit (b)) was polymerized, and the polymerization degree thereof was then confirmed also by the GPC method, so that it was confirmed that a block copolymer having a desired polymerization degree and a desired average molecular weight could be synthesized.

<Unit Ratio>

The unit ratio of a block copolymer was calculated by obtaining the ratio between the polymerization unit (a) and the polymerization unit (b) according to $^1$H-NMR.

<Polymerization Degree of Sugar-Derived Unit(s)>

The polymerization degree of sugar-derived unit(s) was measured before the synthesis of a block copolymer. First, a solution containing the polymerization unit (a) was kept at 50° C., and was centrifuged at 15000 rpm for 15 minutes to remove insoluble matters. Thereafter, the amount of total sugar and the amount of reducing sugar (both relative to xylose) in the supernatant were measured. The amount of total sugar was divided by the amount of reducing sugar to calculate an average polymerization degree.

On the other hand, when the polymerization degree of sugar-derived unit(s) was measured after the synthesis of a block copolymer, the integrated value of a sugar chain-derived peak (around 3.3-5.5 ppm) and the integrated value of other component-derived peak of the polymerization unit (a) were calculated according to $^1$H-NMR, and the average polymerization degree was then calculated based on the ratio of individual integrated values.

<Content Rate of Sugar Moiety>

The content rate of the sugar moiety was obtained according the following equation:

Content rate of sugar moiety (% by mass)=polymerization degree of sugar-derived unit(s)×molecular weight of sugar×number of units with polymerization unit (a)/weight average molecular weight of block copolymer Herein, the number of units with the polymerization unit (a) was calculated from the weight average molecular weight of the block copolymer, the unit ratio, and the molecular weight of each structural unit.

<Solubility>

The weighed block copolymer (0.1 g) was placed into a sample bottle, and was then stirred, while PGMEA or DMF was gradually added thereto (the maximum amount of the solvent: 19.9 g). The liquid temperature of the solvent was set at 25° C., and when the solution seemed to become transparent by visual observation, it was determined that the block copolymer was dissolved in the solvent. Solubility was calculated from the amount of the solvent added.

Solubility (%)=Mass of block copolymer/solvent amount at time of dissolution×100

<Phase Separation Pattern Size/Phase Separation Evaluation>

A block copolymer (20 mg) was dissolved in 1 mL of PGMEA to obtain a self-assembly composition for pattern formation. This self-assembly composition for pattern formation was spin-coated onto a silicone wafer with a size of 2 inches. The spin-coating was carried out, so that the thickness of the film became 45 nm. This wafer was heated on a hot plate at 170° C. for 3 minutes, and the surface was then observed by SEM.

Upon the observation of the surface by SEM, when the phase-separated structure had a cylinder shape, the diameter of the circle at the cross section of the cylinder was defined as a phase separation pattern size. The phase separation size was defined as a mean value of the maximum length (max) of a straight line passing the center point of the circle and the minimum length (min) of a straight line passing the center point of the circle. Besides, even in a case where the cross section of the cylinder did not have a circle shape, a mean value was calculated from the maximum length (max) of a straight line passing the center point of the cross section and the minimum length (min) of a straight line passing the center point of the circle.

When the phase-separated structure had a lamellar shape, the distance (width) between phases was defined as a phase separation pattern size. When the distance between phases is measured, the width between phases remaining after etching was measured. Also in a case where the phase-separated structure had a lamellar shape, a mean value of the maximum length (max) of the width between phases and the minimum length (min) of a straight chain passing the center of the circle was defined as a phase separation pattern size.

The observation was carried out, while the cylinder portion having a concave shape was defined as a hole, and the cylinder portion having a convex shape was defined as a pillar.

TABLE 1

| | Block copolymer | Unit ratio (polymerization unit (b):polymerization unit (a)) | Molecular weight | Polymerization degree of sugar-derived unit per constitutional unit | Content rate of sugar unit (mass %) | Solubility in PGMEA | Solubility in DMF | Phase separation pattern size | Pattern shape |
|---|---|---|---|---|---|---|---|---|---|
| Comp. Ex. 1 | PS-PMMA | 7:3 | 19500 | — | 0% | 5.0% | <0.5% | x | — |
| Comp. Ex. 2 | PS-(sugar methacrylate-ran-methyl methacrylate) | 7:3 | 20000 | 1 | 24% | 2.0% | 3.0% | x | — |
| Comp. Ex. 3 | PS-sugar methacrylate | 1:1 | 21000 | 11 | 84% | <0.5% | 0.7% | — | — |
| Ex. 1 | PS-sugar methacrylate | 72:28 | 20000 | 10 | 75% | <0.5% | 1.0% | 20 nm | Cylinder (hole) |
| Ex. 2 | PS-sugar methacrylate | 7:3 | 20000 | 4 | 57% | <0.5% | 3.0% | 19 nm | Cylinder (hole) |
| Ex. 3 | PS-sugar methacrylate | 6:4 | 20000 | 3 | 56% | <0.5% | 3.0% | 18 nm | Lamella |
| Ex. 4 | PS-acetyl sugar methacrylate | 8:2 | 20000 | 10 | 79% | 2.0% | 3.0% | 21 nm | Cylinder (hole) |
| Ex. 5 | PS-acetyl sugar methacrylate | 82:18 | 100000 | 10 | 77% | 1.0% | 2.0% | 53 nm | Cylinder (hole) |
| Ex. 6 | PTMSS-acetyl sugar methacrylate | 8:2 | 100000 | 4 | 51% | 1.0% | 1.0% | 51 nm | Cylinder (hole) |
| Ex. 7 | PTMSS-acetyl sugar styrene | 8:2 | 100000 | 4 | 52% | 3.0% | 1.0% | 54 nm | Cylinder (hole) |
| Ex. 8 | PTMSS-(acetyl sugar styrene-ran-hydroxy styrene) | 8:2 | 110000 | 4 | 26% | 5.0% | 0.8% | 54 nm | Cylinder (hole) |
| Ex. 9 | PS-sugar methacrylate | 1:1 | 20000 | 1 | 33% | 1.0% | 5.0% | 20 nm | Lamella |
| Ex. 10 | PTMSS-acetyl sugar styrene | 1:1 | 13000 | 3 | 70% | 1.0% | 3.0% | 10 nm | Lamella |
| Ex. 11 | PS-acetyl sugar methacrylate | 3:7 | 200000 | 4 | 76% | 1.0% | 2.0% | 40 nm | Cylinder (pillar) |
| Ex. 12 | PS-acetyl sugar methacrylate | 3:7 | 20000 | 1 | 55% | 2.0% | 3.5% | 13 nm | Cylinder (pillar) |
| Ex. 13 | PS-acetyl sugar methacrylate 2 | 1:1 | 20000 | 2 | 72% | 2.0% | 2.0% | 9 nm | Lamella |
| Ex. 14 | PS-(acetyl sugar methacrylate 2-ran-methyl methacrylate) | 7:3 | 230000 | 3 | 30% | 1.5% | 3.0% | 52 nm | Cylinder (hole) |
| Ex. 15 | PS-(sugar methacrylate-ran-methyl methacrylate) | 7:3 | 20000 | 1 | 3% | 2.0% | 2.5% | 18 nm | Cylinder (hole) |

As is found from Table 1, in the case of using self-assembly compositions for pattern formation comprising the block copolymers obtained in the Examples, it was found that favorable phase separation was achieved. In addition, it was also found that, in the Examples, a large pattern with a size of 30 nm or more could be formed, in addition to the formation of a fine patter with a size of 10 nm or less, and thus that the range of applicable pattern size could be widened. Moreover, in the Example, even in a case where the molecular weight of the block copolymer was relatively small, such as 30000 or less, a phase-separated structure could be formed.

In contrast, in Comparative Examples 1 and 2, the self-assembly composition was applied onto a substrate and was then heated for 5 minutes in a phase separation experiment, and as a result, phase separation was not found by observation according to SEM. Thus, after completion of the etching, an inner space could not be obtained. In Comparative Example 3, the block copolymer was not dissolved in the solvent, and thus, a self-assembly composition for pattern formation could not be formed. Accordingly, the formation of a phase-separated structure could not be evaluated.

REFERENCE SIGNS LIST

1 SELF-ASSEMBLY COMPOSITION FOR PATTERN FORMATION
10 BLOCK COPOLYMER
50 GUIDE HOLE
55 HOLE PART
60 GUIDE PATTERN
62 POST GUIDE
70 SUBSTRATE
P PHASE
Q PHASE

The invention claimed is:
1. A self-assembly composition for pattern formation, which comprises a block copolymer comprising
a polymerization unit (a) having at least one selected from a structure represented by the following formula (103) and a structure represented by the following formula (104), and
a polymerization unit (b) having a structure represented by the following formula (105), wherein
the content rate of a sugar moiety in the block copolymer is 3% by mass or more and 80% by mass or less based on the total mass of the block copolymer:

[Formula 1]

Formula (103)

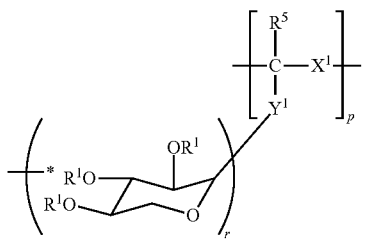

[Formula 2]

Formula (104)

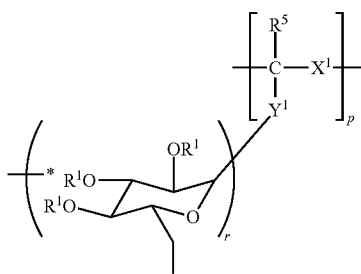

[Formula 3]

Formula (105)

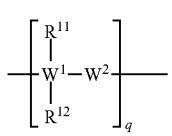

wherein, in the formulae (103) and (104), $R^1$ each independently represents a hydrogen atom, an alkyl group, an acyl group, an aryl group, or a phosphoryl group, and a plurality of $R^1$ may be identical to or different from one another; $R^5$ represents a hydrogen atom or an alkyl group, and a plurality of $R^5$ may be identical to or different from one another; $X^1$ and $Y^1$ each independently represent a single bond or a linking group, a plurality of $X^1$ may be identical to or different from one another, and a plurality of $Y^1$ may be identical to or different from one another; p represents an integer of 2 or more and 1500 or less, r represents an integer of 0 or more, and at least one of a plurality of r represents an integer of 1 or more; and the symbol * represents a binding site with any one of $R^1$, when r represents 2 or more, or represents a binding site with any one oxygen atom to which $R^1$ binds, instead of $R^1$; and in the formula (105), $W^1$ represents a carbon atom or a silicon atom, and a plurality of $W^1$ may be identical to or different from one another; $W^2$ represents —$CR_2$—, —O—, —S—, or —$SiR_2$— (provided that R represents a hydrogen atom or an alkyl group containing 1 to 5 carbon atoms, and a plurality of R may be identical to or different from one another), and a plurality of $W^2$ may be identical to or different from one another; $R^{11}$ represents a hydrogen atom, a methyl group, or a hydroxyl group, and a plurality of $R^{11}$ may be identical to or different from one another; $R^{12}$ represents a phenyl group; and q represents an integer of 2 or more and 3000 or less.

2. The self-assembly composition for pattern formation according to claim 1, wherein solubility of the block copolymer in at least one selected from propylene glycol monomethyl ether acetate (PGMEA) and dimethylformamide (DMF) is 0.8% by mass or more.

3. The self-assembly composition for pattern formation according to claim 1, wherein the r represents an integer of 0 or more, and at least one of a plurality of r represents an integer of 1 or more and 10 or less.

4. The self-assembly composition for pattern formation according to claim 1, which further comprises an organic solvent.

5. The self-assembly composition for pattern formation according to claim 1, which further comprises an ionic liquid.

6. A pattern forming method, comprising
applying the self-assembly composition for pattern formation according to claim 1 onto a substrate, so as to form a self-assembly film according to self-assembly phase separation, and
subjecting to etching.

7. The pattern forming method according to claim 6, wherein the etching is a dry etching.

8. The pattern forming method according to claim 6 which further comprises forming a guide pattern on the substrate before forming the self-assembly film.

9. A self-assembly composition for pattern formation, which comprises a block copolymer comprising
a polymerization unit (a) having a structure represented by the following formula (103), and
a polymerization unit (b) having a structure represented by the following formula (105), wherein the content rate of a sugar moiety in the block copolymer is 3% by mass or more and 80% by mass or less based on the total mass of the block copolymer:

[Formula 1]

Formula (103)

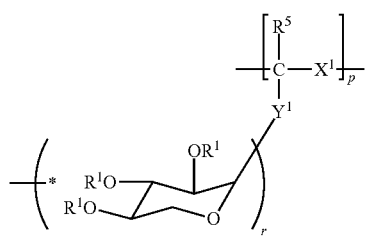

[Formula 3]

Formula (105)

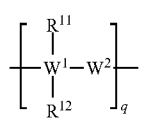

wherein, in the formula (103), $R^1$ each independently represents a hydrogen atom, an alkyl group, an acyl group, an aryl group, or a phosphoryl group, and a plurality of $R^1$ may be identical to or different from one another; $R^5$ represents a hydrogen atom or an alkyl group, and a plurality of $R^5$ may be identical to or different from one another; $X^1$ and $Y^1$ each independently represent a single bond or a linking group, a plurality of $X^1$ may be identical to or different from one another, and a plurality of $Y^1$ may be identical to or different from one another; p represents an integer of 2 or more and 1500 or less, r represents an integer of 0 or more, and at least one of a plurality of r represents an integer of 1 or more; and the symbol * represents a binding site with any one of $R^1$, when r represents 2 or more, or represents a binding site with any one oxygen atom to which $R^1$ binds, instead of $R^1$; and in the formula (105), $W^1$ represents a carbon atom or a silicon atom, and a plurality of $W^1$ may be identical to or different from one another; $W^2$ represents —$CR_2$—, —O—, —S—, or —$SiR_2$— (provided that R represents a hydrogen atom or an alkyl group containing 1 to 5 carbon atoms, and a plurality of R may be identical to or different from one another), and a plurality of $W^2$ may be identical to or different from one another; $R^{11}$ represents a hydrogen atom, a methyl group, or a hydroxyl group, and a plurality of $R^{11}$ may be identical to or different from one another; $R^{12}$ represents a phenyl group; and q represents an integer of 2 or more and 3000 or less.

* * * * *